(12) United States Patent
Asfora

(10) Patent No.: US 10,987,144 B2
(45) Date of Patent: Apr. 27, 2021

(54) SCREW FOR JOINT FUSION

(71) Applicant: Asfora IP, LLC, Sioux Falls, SD (US)

(72) Inventor: Wilson Theophilo Asfora, Sioux Falls, SD (US)

(73) Assignee: Asfora IP, LLC, Sioux Falls, SD (US)

( * ) Notice: Subject to any disclaimer, the term of this patent is extended or adjusted under 35 U.S.C. 154(b) by 205 days.

(21) Appl. No.: 16/378,182

(22) Filed: Apr. 8, 2019

(65) Prior Publication Data
US 2019/0231406 A1    Aug. 1, 2019

Related U.S. Application Data

(60) Division of application No. 13/609,201, filed on Sep. 10, 2012, now Pat. No. 10,251,688, which is a
(Continued)

(51) Int. Cl.
*A61B 17/17* (2006.01)
*A61B 17/86* (2006.01)
(Continued)

(52) U.S. Cl.
CPC ........ *A61B 17/864* (2013.01); *A61B 17/1615* (2013.01); *A61B 17/1637* (2013.01); *A61B 17/17* (2013.01); *A61B 17/1757* (2013.01); *A61B 17/3472* (2013.01); *A61B 17/7055* (2013.01); *A61B 17/861* (2013.01); *A61B 17/8811* (2013.01); *A61F 2/30988* (2013.01); *A61B 2017/564* (2013.01); *A61B 2017/922* (2013.01); *A61B 2090/033* (2016.02); *A61B 2090/062* (2016.02); *A61F 2002/30995* (2013.01)

(58) Field of Classification Search
CPC . A61B 17/17; A61B 17/1739; A61B 17/1742; A61B 17/1757; A61B 17/7055; A61B 2019/462
See application file for complete search history.

(56) References Cited

U.S. PATENT DOCUMENTS 1,563,574 A * 12/1925 Jensen ...................... B26F 1/32
                                                              30/358
2,243,718 A *  5/1941 Moreira ............. A61B 17/1615
                                                              606/80
(Continued)

FOREIGN PATENT DOCUMENTS

WO       0112088 A1    2/2001
WO    2009029056 A1    3/2009
WO    2014026134 A2    2/2014

OTHER PUBLICATIONS

IFuse Implant System, 2012. http://si-bone.co.
(Continued)

*Primary Examiner* — Zade Coley
(74) *Attorney, Agent, or Firm* — Fox Rothschild LLP

(57) ABSTRACT

Techniques for joint fusion are described, including a screw comprising a head having a partially flat surface and an opening for receiving a screwdriver tip, the head able to fit within a drill guide, a tip having another opening, a shaft extending from the head to the tip, the shaft having a plurality of holes and a thread on an external surface of the shaft, and a cannula within the shaft extending from the opening to the another opening.

12 Claims, 26 Drawing Sheets

Related U.S. Application Data continuation of application No. 13/571,126, filed on Aug. 9, 2012, now Pat. No. 9,295,488.

(51) Int. Cl.

| | | |
|---|---|---|
| *A61B 17/16* | (2006.01) | |
| *A61B 17/70* | (2006.01) | |
| *A61B 17/34* | (2006.01) | |
| *A61B 17/88* | (2006.01) | |
| *A61F 2/30* | (2006.01) | |
| *A61B 90/00* | (2016.01) | |
| *A61B 17/56* | (2006.01) | |
| *A61B 17/92* | (2006.01) | |

(56) References Cited

U.S. PATENT DOCUMENTS

| | | | |
|---|---|---|---|
| 2,943,624 A * | 7/1960 | Alquist | A61M 5/31591 604/210 |
| 3,756,390 A * | 9/1973 | Abbey | A61M 5/284 206/219 |
| 3,844,318 A * | 10/1974 | Raia | A61M 5/1782 141/27 |
| 3,844,381 A | 10/1974 | Raia | |
| 3,867,932 A * | 2/1975 | Huene | A61B 17/17 606/80 |
| 4,018,223 A * | 4/1977 | Ethington | A61M 5/31525 604/207 |
| 4,248,225 A * | 2/1981 | Moore | A61M 5/1782 310/17 |
| 4,257,411 A | 3/1981 | Cho | |
| 4,306,866 A | 12/1981 | Weissman | |
| 4,325,373 A | 4/1982 | Slivenko | |
| 4,341,206 A | 7/1982 | Perrett | |
| 4,368,736 A | 1/1983 | Kaster | |
| 4,434,815 A | 3/1984 | Flaherty | |
| 4,465,478 A * | 8/1984 | Sabelman | A61M 5/315 604/224 |
| 4,489,766 A * | 12/1984 | Montada | A61M 5/1782 141/27 |
| 4,563,178 A * | 1/1986 | Santeramo | A61M 5/1782 141/27 |
| 4,653,481 A | 3/1987 | Howland | |
| 4,710,075 A | 12/1987 | Davison | |
| 4,811,511 A | 3/1989 | Beretta | |
| 4,865,025 A | 9/1989 | Buzzi | |
| 4,865,028 A | 9/1989 | Buzzi | |
| 5,004,255 A | 4/1991 | Briggs | |
| 5,019,080 A | 5/1991 | Hemer | |
| 5,115,816 A * | 5/1992 | Lee | A61M 5/1782 600/562 |
| 5,141,513 A | 8/1992 | Fortune | |
| 5,209,753 A | 5/1993 | Biedermann | |
| 5,234,431 A | 8/1993 | Keller | |
| 5,234,434 A | 8/1993 | Goble | |
| 5,242,444 A * | 9/1993 | MacMillan | A61B 17/1757 606/60 |
| 5,261,909 A | 11/1993 | Sutterlin | |
| 5,334,205 A * | 8/1994 | Cain | A61B 17/1739 606/86 R |
| 5,336,224 A | 8/1994 | Selman | |
| 5,397,363 A | 3/1995 | Gelbard | |
| D357,534 S * | 4/1995 | Hayes | D24/140 |
| 5,468,233 A * | 11/1995 | Schraga | A61M 5/1782 141/27 |
| 5,474,555 A | 12/1995 | Puno | |
| 5,505,731 A | 4/1996 | Tornier | |
| 5,549,607 A | 8/1996 | Olson | |
| 5,575,793 A | 11/1996 | Carls | |
| 5,591,207 A | 1/1997 | Coleman | |
| 5,628,740 A | 5/1997 | Mullane | |
| 5,634,925 A | 6/1997 | Urbanski | |
| 5,649,930 A | 7/1997 | Kertzner | |
| 5,653,708 A | 8/1997 | Howland | |
| 5,661,923 A | 9/1997 | Fellowes | |
| 5,676,545 A | 10/1997 | Jones | |
| 5,676,703 A | 10/1997 | Gelbard | |
| 5,700,268 A | 12/1997 | Bertin | |
| 5,725,581 A | 3/1998 | Branemark | |
| 5,735,898 A | 4/1998 | Branemark | |
| 5,743,916 A * | 4/1998 | Greenberg | A61B 17/02 606/102 |
| 5,766,179 A | 6/1998 | Facciolo | |
| 5,766,254 A | 6/1998 | Gelbard | |
| 5,830,052 A | 11/1998 | Wadsworth | |
| D411,009 S | 6/1999 | Asfora | |
| 5,921,995 A | 7/1999 | Kleshinski | |
| 5,947,967 A | 9/1999 | Barker | |
| 5,980,540 A | 11/1999 | Bruce | |
| 6,001,098 A | 12/1999 | Metz-Stavenhagen | |
| 6,004,322 A | 12/1999 | Bernstein | |
| 6,030,162 A | 2/2000 | Huebner | |
| 6,036,705 A | 3/2000 | Nash | |
| 6,050,997 A | 4/2000 | Mullane | |
| 6,135,772 A | 10/2000 | Jones | |
| 6,149,686 A | 11/2000 | Kuslich | |
| 6,176,861 B1 | 1/2001 | Bernstein | |
| 6,206,922 B1 | 3/2001 | Zdeblick | |
| 6,261,288 B1 | 7/2001 | Jackson | |
| 6,264,658 B1 | 7/2001 | Lee | |
| 6,287,313 B1 | 9/2001 | Sasso | |
| 6,287,343 B1 | 9/2001 | Kuslich | |
| 6,357,951 B1 | 3/2002 | Tibbetts | |
| 6,375,658 B1 | 4/2002 | Hangody | |
| 6,379,357 B1 | 4/2002 | Bernstein | |
| 6,391,058 B1 | 5/2002 | Kuslich | |
| 6,413,257 B1 | 7/2002 | Lin | |
| 6,432,109 B1 | 8/2002 | Letendart | |
| 6,451,021 B1 | 9/2002 | Ralph | |
| 6,471,724 B2 | 10/2002 | Zdeblick | |
| 6,494,611 B2 * | 12/2002 | Edwards | B01F 11/0008 366/209 |
| 6,517,542 B1 | 2/2003 | Papay | |
| 6,547,791 B1 | 4/2003 | Buhren | |
| 6,554,830 B1 | 4/2003 | Chappius | |
| 6,562,046 B2 | 5/2003 | Sasso | |
| 6,565,572 B2 | 5/2003 | Chappius | |
| 6,592,585 B2 | 7/2003 | Lee | |
| 6,604,945 B1 | 8/2003 | Jones | |
| 6,623,485 B2 | 9/2003 | Doubler | |
| 6,626,912 B2 * | 9/2003 | Speitling | B01F 11/0025 366/209 |
| 6,695,851 B2 | 2/2004 | Zdeblick | |
| 6,706,045 B2 | 3/2004 | Lin | |
| 6,730,092 B2 | 5/2004 | Songer | |
| 6,739,872 B1 | 5/2004 | Turri | |
| 6,755,830 B2 | 6/2004 | Minfelde | |
| 6,755,835 B2 | 6/2004 | Schultheiss | |
| 6,761,722 B2 * | 7/2004 | Cole | A61B 17/0401 606/74 |
| 6,793,657 B2 | 9/2004 | Lee | |
| 6,814,738 B2 * | 11/2004 | Naughton | A61B 17/88 606/100 |
| 6,827,719 B2 | 12/2004 | Ralph | |
| 6,840,940 B2 | 1/2005 | Ralph | |
| 6,887,242 B2 | 5/2005 | Doubler | |
| 6,951,562 B2 | 10/2005 | Zwirnmann | |
| 6,969,193 B1 | 11/2005 | Pigg | |
| 7,033,363 B2 * | 4/2006 | Powell | A61B 17/1615 606/104 |
| 7,090,675 B2 | 8/2006 | Songer | |
| 7,160,311 B2 | 1/2007 | Blatter | |
| 7,166,073 B2 | 1/2007 | Ritland | |
| 7,198,627 B2 | 4/2007 | Bagga | |
| 7,291,152 B2 | 11/2007 | Abdou | |
| 7,335,201 B2 | 2/2008 | Doubler | |
| 7,338,490 B2 | 3/2008 | Ogilvie | |
| 7,354,442 B2 | 4/2008 | Sasso | |
| 7,377,922 B2 | 5/2008 | Barker | |
| 7,472,630 B1 | 1/2009 | Velluzzi | |
| 7,527,611 B2 * | 5/2009 | Sweeney | A61B 17/7061 604/264 |
| 7,569,058 B2 | 8/2009 | Zwirnmann | |

(56) References Cited

U.S. PATENT DOCUMENTS

| | | | |
|---|---|---|---|
| 7,575,572 B2 | 8/2009 | Sweeney | |
| 7,575,579 B2 | 8/2009 | Taras | |
| 7,591,851 B2 | 9/2009 | Winslow | |
| 7,601,170 B2 | 10/2009 | Winslow | |
| 7,604,667 B2 | 10/2009 | DeSmet | |
| 7,608,062 B2 | 10/2009 | Sweeney | |
| 7,611,495 B1 * | 11/2009 | Gianturco | A61M 5/31501 604/207 |
| 7,618,443 B2 | 11/2009 | Abdou | |
| 7,621,958 B2 | 11/2009 | Zdeblick | |
| 7,625,408 B2 | 12/2009 | Gupta | |
| 7,635,366 B2 | 12/2009 | Abdou | |
| 7,717,919 B2 | 5/2010 | Asse | |
| 7,717,947 B1 | 5/2010 | Wilberg | |
| 7,722,646 B2 | 5/2010 | Ralph | |
| 7,740,016 B1 | 6/2010 | Pigg | |
| 7,740,649 B2 | 6/2010 | Mosca | |
| 7,763,050 B2 | 7/2010 | Winslow | |
| 7,771,143 B2 | 8/2010 | Bharadwaj | |
| 7,776,090 B2 | 8/2010 | Winslow | |
| 7,846,093 B2 | 12/2010 | Gorek | |
| 7,862,588 B2 | 1/2011 | Abdou | |
| 7,905,924 B2 | 3/2011 | White | |
| 7,909,859 B2 | 3/2011 | Mosca | |
| 7,918,896 B2 | 4/2011 | DeSmet | |
| 7,938,832 B2 * | 5/2011 | Culbert | A61B 17/1757 606/86 A |
| 7,942,909 B2 | 5/2011 | Hammill, Sr. | |
| 7,942,910 B2 | 5/2011 | Doubler | |
| 7,942,911 B2 | 5/2011 | Doubler | |
| 7,947,065 B2 | 5/2011 | Hammill, Sr. | |
| 7,951,173 B2 | 5/2011 | Hammill, Sr. | |
| 7,981,117 B2 | 7/2011 | Newton | |
| 7,985,258 B2 | 7/2011 | Zdeblick | |
| 8,006,700 B2 | 8/2011 | Demopulos | |
| 8,016,861 B2 | 9/2011 | Mitchell | |
| 8,021,397 B2 | 9/2011 | Farris | |
| 8,029,216 B2 | 10/2011 | Guy | |
| 8,029,540 B2 | 10/2011 | Winslow | |
| 8,048,125 B2 | 11/2011 | Mitchell | |
| 8,057,523 B2 | 11/2011 | Densford | |
| 8,062,270 B2 | 11/2011 | Sweeney | |
| 8,075,591 B2 | 12/2011 | Ludwig | |
| 8,075,603 B2 | 12/2011 | Hammill, Sr. | |
| 8,100,944 B2 | 1/2012 | Lauryssen | |
| 8,118,838 B2 | 2/2012 | Winslow | |
| 8,128,660 B2 | 3/2012 | Mitchel | |
| 8,172,877 B2 | 5/2012 | Winslow | |
| 8,197,481 B2 | 6/2012 | Zwirnmann | |
| 8,197,518 B2 | 6/2012 | Hammill, Sr. | |
| 8,231,630 B2 | 7/2012 | Long | |
| 8,241,334 B2 | 8/2012 | Butler | |
| D667,548 S | 9/2012 | Brannon | |
| 8,298,138 B2 | 10/2012 | Gorek | |
| 8,303,593 B2 | 11/2012 | Simon | |
| 8,303,602 B2 | 11/2012 | Biedermann | |
| 8,308,732 B2 | 11/2012 | Millett | |
| 8,308,776 B2 | 11/2012 | Abdou | |
| 8,317,862 B2 * | 11/2012 | Troger | A61B 17/1764 623/13.11 |
| 8,382,808 B2 | 2/2013 | Wilberg | |
| 8,398,689 B2 | 3/2013 | Abdou | |
| 8,425,530 B2 | 4/2013 | Winslow | |
| 8,465,530 B2 | 6/2013 | Hammill, Sr. | |
| 8,506,601 B2 | 8/2013 | Gephart | |
| 8,543,188 B2 | 9/2013 | von Jako | |
| 8,545,500 B2 | 10/2013 | Babat | |
| 8,545,531 B2 | 10/2013 | Geist | |
| 8,545,538 B2 | 10/2013 | Abdou | |
| 8,548,563 B2 | 10/2013 | Simon | |
| 8,549,732 B2 | 10/2013 | Burg | |
| 8,549,888 B2 | 10/2013 | Isaacs | |
| 8,551,092 B2 | 10/2013 | Morgan | |
| 8,551,106 B2 | 10/2013 | Harrold | |
| 8,551,140 B2 | 10/2013 | Denham | |
| 8,551,141 B2 | 10/2013 | Gephart | |
| 8,551,142 B2 | 10/2013 | Altarac | |
| 8,551,144 B2 | 10/2013 | Youssef | |
| 8,551,146 B2 | 10/2013 | Kumar | |
| 8,551,171 B2 | 10/2013 | Johnson | |
| 8,551,180 B2 | 10/2013 | Shultz | |
| 8,556,074 B2 | 10/2013 | Turner | |
| 8,556,797 B2 | 10/2013 | Weadock | |
| 8,556,860 B2 | 10/2013 | Stratton | |
| 8,556,895 B2 | 10/2013 | Stern | |
| 8,556,901 B2 | 10/2013 | Anthony | |
| 8,556,903 B2 | 10/2013 | Miller | |
| 8,556,904 B2 | 10/2013 | Rezach | |
| 8,556,937 B2 | 10/2013 | Ludwig | |
| 8,556,938 B2 | 10/2013 | Jackson | |
| 8,556,941 B2 | 10/2013 | Hutchinson | |
| 8,556,942 B2 | 10/2013 | Ziolo | |
| 8,556,944 B2 | 10/2013 | Dube | |
| 8,556,945 B2 | 10/2013 | Orbay | |
| 8,556,947 B2 | 10/2013 | Dorawa | |
| 8,556,949 B2 | 10/2013 | Teisen | |
| 8,556,970 B2 | 10/2013 | Piccirillo | |
| 8,556,974 B2 | 10/2013 | Suh | |
| 8,556,987 B2 | 10/2013 | Hunter | |
| 8,561,616 B2 | 10/2013 | Rousseau | |
| 8,561,617 B2 | 10/2013 | Lindh | |
| 8,562,344 B2 | 10/2013 | Grant | |
| 8,562,652 B2 | 10/2013 | Biedermann | |
| 8,562,655 B2 | 10/2013 | Butler | |
| 8,562,681 B2 | 10/2013 | Shepard | |
| 8,562,682 B2 | 10/2013 | Gill | |
| 8,568,291 B2 | 10/2013 | Ball | |
| 8,568,413 B2 | 10/2013 | Mazur | |
| 8,568,417 B2 | 10/2013 | Petrzelka | |
| 8,568,451 B2 | 10/2013 | Zucherman | |
| 8,568,452 B2 | 10/2013 | Voorhies | |
| 8,568,453 B2 | 10/2013 | Abdou | |
| 8,568,458 B2 | 10/2013 | Matthis | |
| 8,568,462 B2 | 10/2013 | Sixto, Jr. | |
| 8,568,765 B2 | 10/2013 | Ameer | |
| 8,574,273 B2 | 11/2013 | Russell | |
| 8,764,797 B2 | 7/2014 | Dreyfuss | |
| 8,808,337 B2 | 8/2014 | Sweeney | |
| 8,870,836 B2 | 10/2014 | Sweeney | |
| 8,956,369 B2 | 2/2015 | Millett | |
| 9,131,970 B2 | 9/2015 | Kang | |
| 9,173,692 B1 | 11/2015 | Kaloostian | |
| 9,198,702 B2 | 12/2015 | Biederman | |
| 9,271,742 B2 | 3/2016 | Asfora | |
| 9,271,743 B2 | 3/2016 | Asfora | |
| 9,295,488 B2 | 3/2016 | Asfora | |
| 9,326,779 B2 | 5/2016 | Dorawa | |
| 9,326,801 B2 | 5/2016 | Poulos | |
| 9,333,018 B2 | 5/2016 | Russell | |
| 9,445,852 B2 | 9/2016 | Sweeney | |
| 9,504,469 B2 | 11/2016 | Asfora | |
| 9,526,548 B2 | 12/2016 | Asfora | |
| 9,566,100 B2 | 2/2017 | Asfora | |
| 9,616,205 B2 | 4/2017 | Nebosky | |
| 9,642,656 B2 | 5/2017 | Kotuljac | |
| 2001/0001121 A1 | 5/2001 | Lombardo | |
| 2001/0021852 A1 * | 9/2001 | Chappius | A61B 17/864 600/300 |
| 2001/0041902 A1 | 11/2001 | Lepulu | |
| 2002/0038123 A1 | 3/2002 | Visotsky | |
| 2002/0107523 A1 * | 8/2002 | Naughton | A61F 2/4603 606/100 |
| 2002/0123752 A1 | 9/2002 | Schultheiss | |
| 2003/0088251 A1 | 5/2003 | Braun | |
| 2005/0192604 A1 | 9/2005 | Carson | |
| 2005/0256453 A1 * | 11/2005 | Nagamatsu | A61M 25/10182 604/97.02 |
| 2005/0273167 A1 | 12/2005 | Triplett | |
| 2007/0149894 A1 * | 6/2007 | Heske | A61B 17/3421 600/566 |
| 2007/0150003 A1 | 6/2007 | Dreyfuss | |
| 2007/0161985 A1 | 7/2007 | Demakas | |
| 2007/0233123 A1 | 10/2007 | Ahmad | |
| 2007/0233138 A1 | 10/2007 | Figueroa | |

(56) References Cited

U.S. PATENT DOCUMENTS

| | | |
|---|---|---|
| 2007/0239166 A1 | 10/2007 | McGuire |
| 2008/0103506 A1 | 5/2008 | Volpi |
| 2009/0024135 A1 | 1/2009 | Triplett |
| 2009/0024174 A1* | 1/2009 | Stark .................. A61B 17/8625 606/321 |
| 2009/0099602 A1 | 4/2009 | Aflatoon |
| 2009/0192551 A1 | 7/2009 | Cianfrani |
| 2009/0264889 A1 | 10/2009 | Long |
| 2010/0010496 A1* | 1/2010 | Isaza .................. A61B 17/1739 606/96 |
| 2010/0256688 A1* | 10/2010 | Giersch .................. A61B 17/68 606/305 |
| 2010/0262153 A1 | 10/2010 | Millett |
| 2010/0312249 A1 | 12/2010 | Sanders |
| 2011/0060373 A1 | 3/2011 | Russell |
| 2011/0087296 A1* | 4/2011 | Reiley ................ A61B 17/1615 606/303 |
| 2011/0125265 A1 | 5/2011 | Bagga |
| 2011/0137352 A1 | 6/2011 | Biedermann |
| 2011/0213423 A1 | 9/2011 | Biedermann |
| 2011/0213426 A1 | 9/2011 | Yedlicka |
| 2011/0264229 A1* | 10/2011 | Donner .............. A61B 17/7055 623/18.11 |
| 2012/0089195 A1 | 4/2012 | Yedlicka |
| 2012/0221005 A1 | 8/2012 | Corneille |
| 2013/0065698 A1 | 3/2013 | Biedermann |
| 2013/0144344 A1 | 6/2013 | Giancola |
| 2013/0245602 A1 | 9/2013 | Sweeney |
| 2014/0012340 A1 | 1/2014 | Beck |
| 2014/0046381 A1 | 2/2014 | Asfora |
| 2014/0277188 A1 | 9/2014 | Poulos |
| 2015/0230844 A1 | 8/2015 | Ellis |
| 2015/0238203 A1 | 8/2015 | Asfora |
| 2015/0272646 A1 | 10/2015 | Russell |
| 2015/0313658 A1 | 11/2015 | Kolb |
| 2016/0000489 A1 | 1/2016 | Kaloostian |
| 2016/0008044 A1 | 1/2016 | Sweeney |
| 2016/0143671 A1 | 5/2016 | Jimenez |
| 2016/0143679 A1 | 5/2016 | Asfora |
| 2016/0143742 A1 | 5/2016 | Asfora |
| 2016/0151100 A1 | 6/2016 | Biedermann |
| 2016/0220291 A1 | 8/2016 | Russell |
| 2016/0310188 A1 | 10/2016 | Marino |

OTHER PUBLICATIONS

Synthes, Inc., 3.0 mm Cannulated Screws, 2006, USA. https://productlit.synthes.com/prod_support/Product%20Support%20Materials/Technique%20Guides/SUSA/SUTG30CanScrWshJ2675E.pdf.

Synthes, Inc., 4.0 mm Cannulated Screw, 2006, USA. https://productlit.synthes.com/prod_support/Product%20Support%20Materials/Technique%20Guides/SUSA/SUTG40CannScrewJ3270G.pdf D.

* cited by examiner

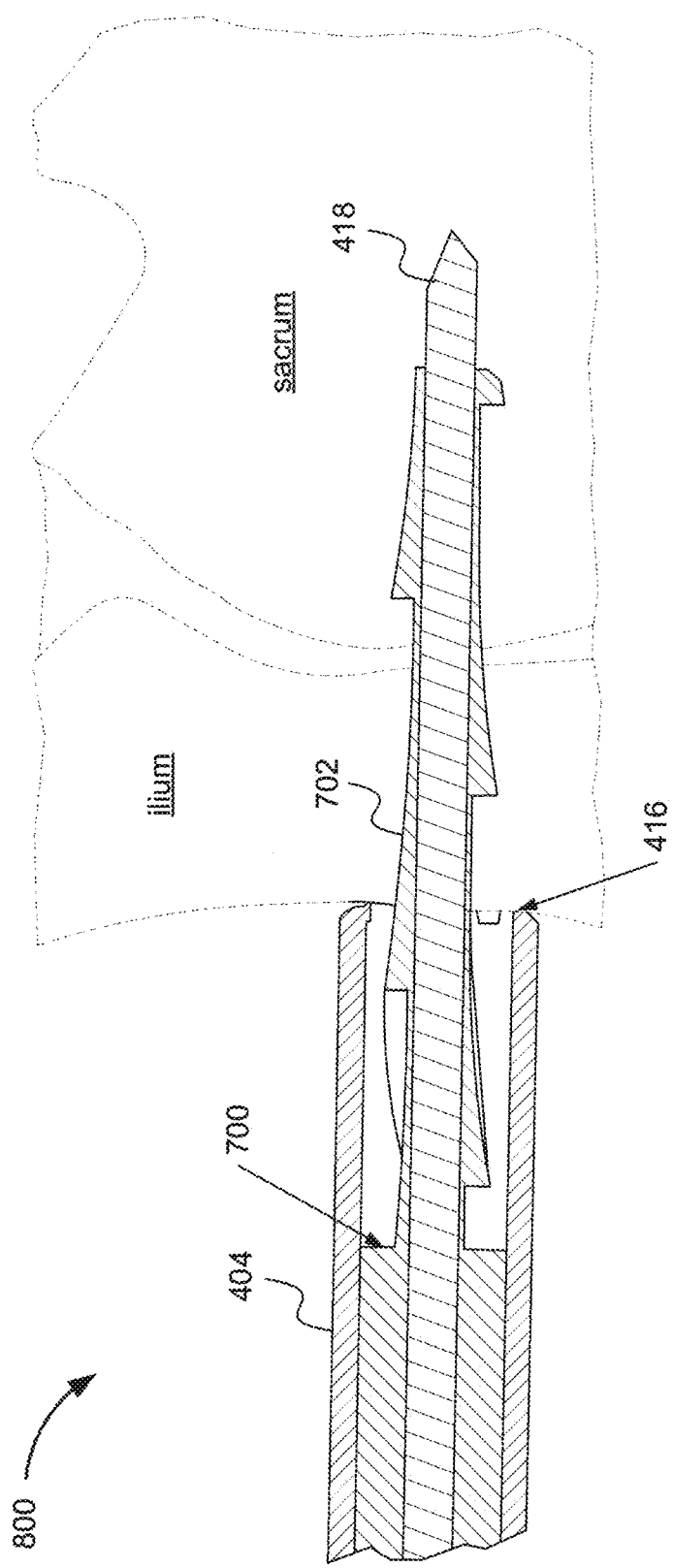

US 10,987,144 B2

SCREW FOR JOINT FUSION

CROSS-REFERENCE TO RELATED APPLICATIONS

This application is a divisional of U.S. patent application Ser. No. 13/609,201, filed Sep. 10, 2012, now U.S. Pat. No. 10,251,688 which is a continuation of U.S. patent application Ser. No. 13/571,126, filed Aug. 9, 2012, now U.S. Pat. No. 9,295,488, which are incorporated by reference herein in their entirety for all purposes.

FIELD

The present invention relates generally to orthopedic surgery. More specifically, techniques associated with a screw for joint fusion are described.

BACKGROUND

Stress across joints generally is a common cause of pain. Stress across the sacroiliac joint is a common source of lower back pain. Such sacroiliac joint stress, including sacroiliac joint disruptions (i.e., separations) and degenerative sacroiliitis (i.e. inflammation), can result from lumbar fusion, trauma, postpartum, heavy lifting, arthritis, or unknown causes. Sacroiliac joint fixation or arthrodesis is sometimes recommended for skeletally mature patients with severe, chronic sacroiliac joint pain or acute trauma in the sacroiliac joint.

Conventional solutions for stabilizing joints and relieving pain in joints typically include the insertion of an implant, such as a metal screw, rod or bar, laterally across the joint. However, conventional solutions can involve invasive surgical procedures. Furthermore, even more minimally invasive procedures have drawbacks. One drawback of conventional solutions for sacroiliac joint fixation is the inability to deliver materials, such as osteogenic, osteoconductive, other bone regenerative materials, antibiotics, steroids, and other joint treatment materials (i.e., for inflammation or infections), to the bones through implants and an implantation procedure that is minimally invasive. Another drawback of conventional implants for sacroiliac joint fixation is that they do not allow for bone growth into and through the implant for true fusion of the joint. Finally, conventional implantation solutions do not provide methods for delivering such joint stress treatment materials through the implant at a later time (i.e., post-implantation).

Thus, techniques for joint fusion without the limitations of conventional techniques are needed.

BRIEF DESCRIPTION OF THE DRAWINGS

Various embodiments or examples (collectively "examples") of the invention are disclosed in the following detailed description and the accompanying drawings:

FIG. 8 illustrates a cross-section view of an exemplary sacroiliac joint with an applied guide pin, drill bit and drill guide;

DETAILED DESCRIPTION

Figure 1A:
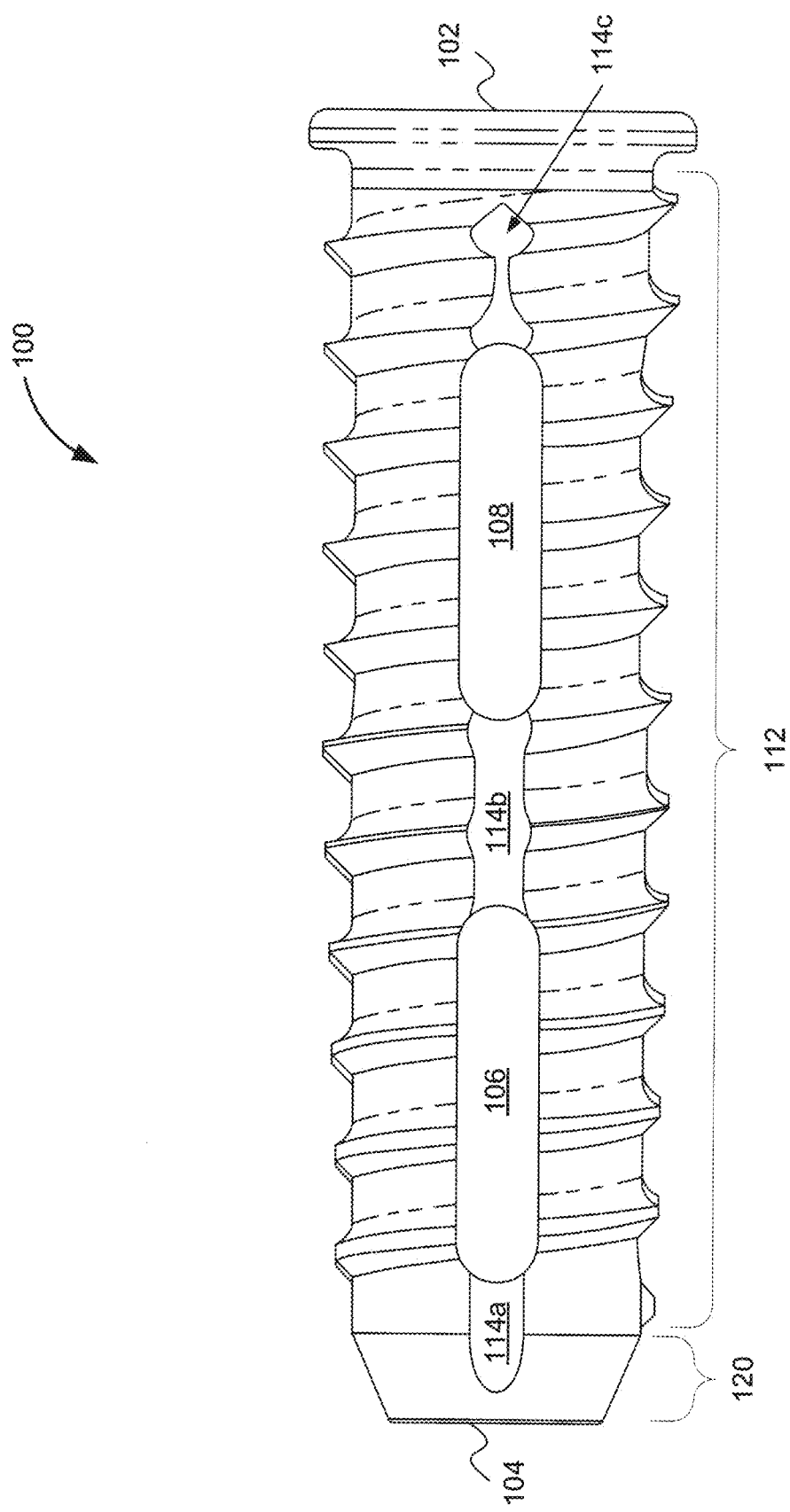
FIGS. 1A-1C illustrate a side view, a perspective view and a cross-section view, respectively, of an exemplary screw for joint fusion.

Various embodiments or examples may be implemented in numerous ways, including as a system, a process or an apparatus. In general, operations of disclosed processes may be performed in an arbitrary order, unless otherwise provided in the claims. A detailed description of one or more examples is provided below along with accompanying figures. The detailed description is provided in connection with such examples, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

Techniques for joint fusion are described, including systems, apparatuses and processes for fusing a joint. Systems and apparatuses for fusing a joint include a screw (i.e., a cannulated screw), a drill guide assembly, a guide pin, a striker tube, a depth gauge, a cannulated drill bit (e.g., an adjustable cannulated drill bit that employs a stop collar), a driver, a parallel spacer instrument, a packing plunger assembly, and a plunger distance tool. As used herein, the term "cannulated" refers to having a cannula, or a hollow shaft. In some examples, the screw may be inserted or implanted into tissue (e.g., bone, cartilage, or other tissue in the joint). As used herein, the term "implant" or "implantation" refers to inserting or insertion into a part of a body. For example, a screw may be implanted into a joint (i.e., a sacroiliac joint). In some examples, a screw may have a cannula in which materials may be packed. Such materials may include osteogenic compounds (e.g., bone morphogenetic protein, or other osteogenic compounds that may ossify tissue in the joint), osteoconductive materials (e.g., demineralized bone, hydroxyappatite, or other material that promotes bone growth), antibiotics, steroids, contrast materials, or other materials that may beneficial to fusing the joint, treating inflammation or other conditions in the joint, or enabling the visualization of the area within and adjacent to an implanted screw. In some examples, the screw may have slots, perforations, openings or orifices (collectively "slots") along the wall of its shaft to allow the material packed inside the cannula of the screw to contact (e.g., touch, seep into, affect, communicate with, or otherwise physically contact) tissue adjacent to, surrounding, or even within, the screw. In some examples, various tools may be used to insert a screw into a location on a joint, and to prepare the location for the insertion procedure. Such tools may include a drill guide assembly, which may comprise a drill guide and a pin sleeve; a guide pin; a striker tube; a depth gauge; a cannulated drill bit (e.g., an adjustable cannulated drill bit with a stop collar); a driver; a parallel spacer instrument; a packing plunger assembly, which may comprise a packing tube, a plunger and a loading port; a plunger distance tool; and other tools.

In some examples, a guide pin may be inserted first into a joint at a desired location in a lateral position across the joint. In some examples, a drill guide assembly may be used, along with the guide pin, to guide the preparation (i.e., drilling) of a pilot hole as well as to guide insertion of a cannulated screw or other implant. In some examples, a cannulated drill bit may be used with the drill guide to drill the pilot hole. In some examples, a stop collar may be coupled to the cannulated drill bit to assist with drilling the pilot hole to the desired depth. In some examples, a driver or screwdriver may be used to insert the screw into the pilot hole. The terms "driver" and "screwdriver" are used herein interchangeably to refer to a tool with a tip configured to engage the head of a screw, the tool being useful for rotating a screw, or otherwise manipulating the screw, to drive the screw into place in a joint. In some examples, a parallel spacer instrument may be used to space another guide pin in preparation for insertion of another screw. In some examples, a packing plunger assembly may be used to pack the screw with the above-mentioned materials. The packing plunger may be used to pack materials into the screw either or both pre- and post-insertion of the screw into the joint, and may be used with or without the drill guide assembly.

Figure 1B:
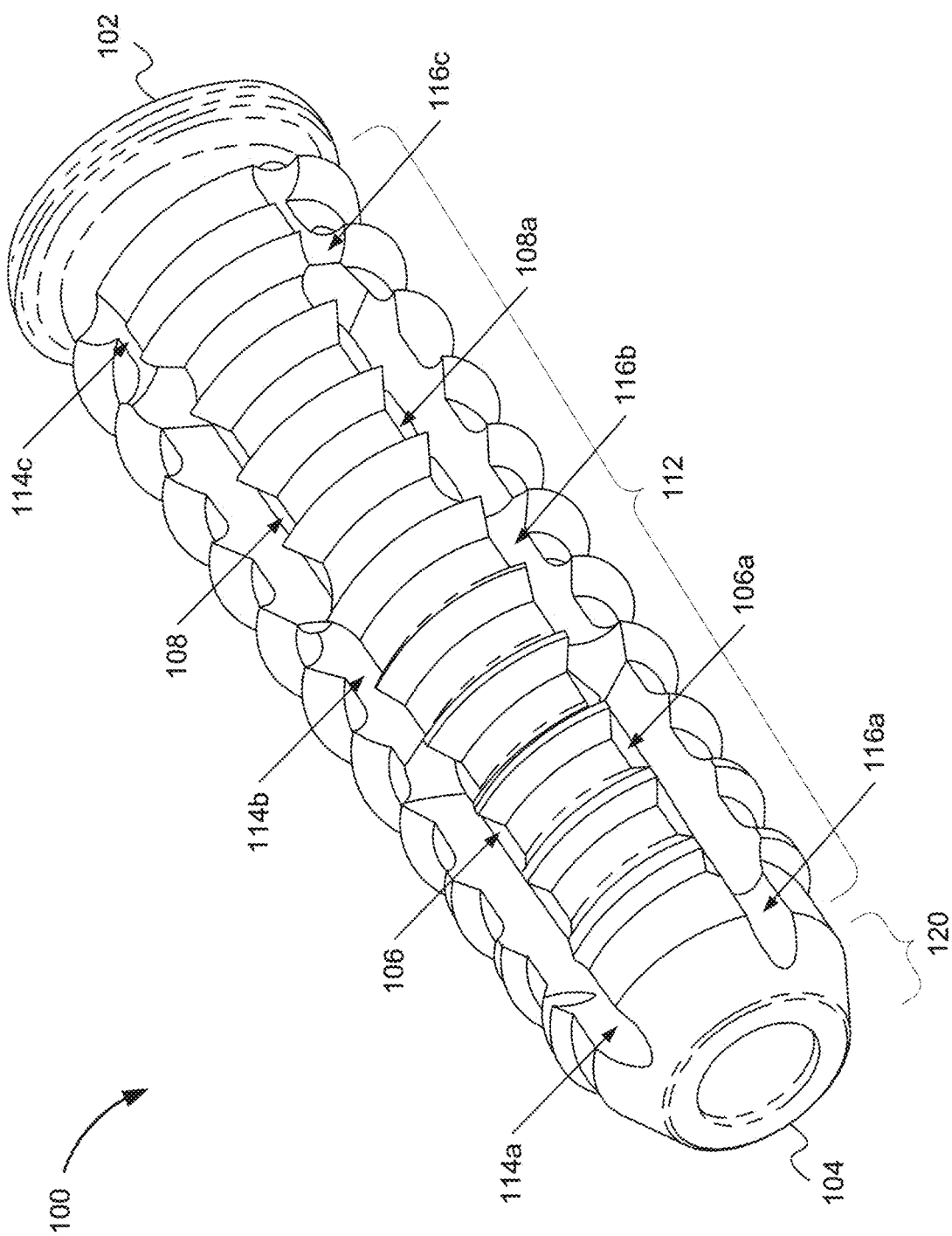
Figure 1C:
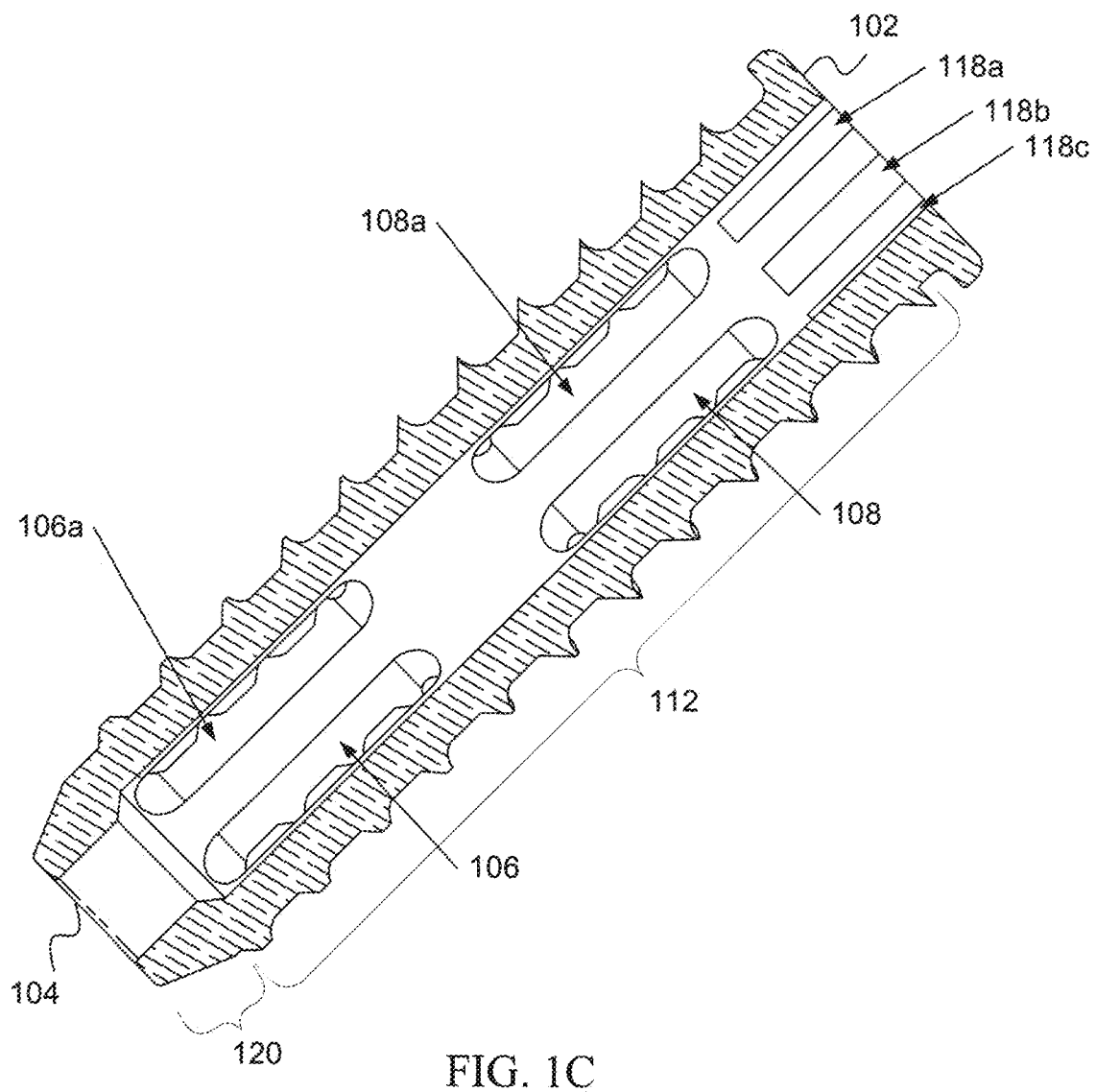

FIGS. 1A-1C illustrate a side view, a perspective view and a cross-section view, respectively, of an exemplary screw for joint fusion. Here, screw 100 includes head 102, tip 104, slots 106-108 and 106a-108a, threads 112, shaft grooves 114a-114c and 116a-116c, head grooves 118a-118c, and tapered end 120. Like-numbered and named elements in these views may describe the same or substantially similar elements. In some examples, screw 100 may be fabricated, manufactured, or otherwise formed, using various types of medical grade material, including stainless steel, plastic, composite materials, or alloys (e.g., Ti-6Al-4V ELI, another medical grade titanium alloy, or other medical grade alloy) that may be corrosion resistant and biocompatible (i.e., not having a toxic or injurious effect on tissue into which it is implanted). In some examples, threads 112 may be a helical ridge wrapped around an outer surface of screw 100's shaft. In some examples, screw 100 may be cannulated and may have a hollow shaft that extends from head 102 to tip 104. Screw 100 may vary in length (e.g., ranging from approximately 25 mm to 50 mm, or longer or shorter) to accommodate size and geometric variance in a joint. Other dimensions of screw 100, including major and minor diameters of threads 112 (see, e.g., FIG. 3B), also may vary to accommodate size and geometric variance in a joint. In one example, head 102 may be 9.5 mm in diameter and threads 112 may have a major diameter of 9 mm and a minor (i.e., root) diameter of 7.4 mm. In other examples, head 102 may have a different diameter and threads 112 may have different major and minor diameters. In some examples, an outer surface of screw 100's shaft may taper from head 102 to tapered end 120, and thus threads 112 also may taper (i.e., be a tapered thread) from head 102 to tapered end 120 (e.g., having a range of major and minor diameters from head 102 to tapered end 120). In some examples, the tapering of threads 112, as well as tapered end 120, may aid in guiding the screw through a pilot hole. In other examples, head 102 and threads 112 may be sized to fit within a tool or instrument, for example, a drill guide, as described below.

In some examples, screw 100's hollow shaft, or cannula, may be accessed (i.e., for packing material into) through an opening in head 102. In some examples, head 102 may have a flat or partially flat surface (e.g., pan-shaped with rounded edge, unevenly flat, or other partly flat surface). In other examples, head 102 may have a different shape (e.g, dome, button, round, truss, mushroom, countersunk, oval, raised, bugle, cheese, fillister, flanged, or other screw head shape). In some examples, the opening in head 102 may have a TORX® or TORX®-like shape (i.e., six-point or six-lobed shape) (see FIG. 3A) configured to receive the tip of a TORX® or TORX®-like screwdriver (e.g., driver 902). For example, screw 100 may include head grooves 118a-118c, which may start at head 102 and extend linearly into the cannula of screw 100 to receive complementary lobes on the end of a screwdriver. For a TORX® or TORX®-like opening there may be six (6) total head grooves, including for example head grooves 118a-118c, to receive the complementary lobes on the tip of a TORX® or TORX®-like driver. In some examples, as shown in FIG. 1C, the opening in head 102 may be contiguous with, and form a top end of, screw 100's cannula. For example, the opening may provide access to the cannula, for example, to pack material into the screw.

As described herein, such materials may include osteogenic compounds (e.g., bone morphogenetic protein, or other osteogenic compounds that may ossify tissue), osteoconductive materials (e.g., demineralized bone, hydroxyappatite, or other material that promotes bone growth), antibiotics, steroids, contrast materials, or other materials that may beneficial to fusing the joint, treating inflammation or other conditions in the joint, or enabling the visualization of the area within and adjacent to the screw. For example, an osteogenic compound, such as bone morphogenetic protein or other compounds, may be packed into screw 100's cannula such that, when screw 100 is inserted into a joint or traverses through a joint (e.g., a sacroiliac joint), the osteogenic compound, for example through holes or openings (e.g., slots 106-108 and 106a-108a) may come into contact with tissue in the joint adjacent to or surrounding screw 100, and ossify the tissue to fuse the joint across and through the screw. In some examples, the osteogenic compound may enter the joint and may fill the joint, partially or entirely. In other examples, an osteoconductive materials, such as demineralized bone or hydroxyappatite or other materials, may be packed into screw 100's cannula such that, when screw 100 is inserted into a joint, the osteoconductive material may come into contact with tissue in the joint adjacent to or surrounding screw 100, for example through slots 106-108 and 106a-108a, and promote bone growth into the screw and the joint to fuse the joint across and through the screw. In still other examples, a substance for treating sacroiliitis, such as steroids or antibiotics or other substances, may be packed into screw 100's cannula such that, when screw 100 is inserted into the joint, the substance may come into contact with tissue in the joint adjacent to or surrounding screw 100, for example through slots 106-108 and 106a-108a, and treat the inflamed joint tissue. In yet other examples, a contrast material may be packed into screw 100's cannula such that, when screw 100 is inserted into the joint, the contrast material within screw 100, and in some examples absorbed by tissue adjacent to or surrounding screw 100, may be viewed using visualization techniques (e.g., x-ray, fluoroscope, ultrasound, or other visualization technique). In still other examples, different materials may be packed into screw 100 for different purposes. In yet other examples, the above-described materials may also come into contact with tissue adjacent to, or surrounding, screw 100 through an opening at tip 104. As described herein, screw 100 may be packed with material prior to being inserted into the joint, and may also be packed after insertion into the joint. Also as described herein, such materials may be packed into screw 100 using a packing plunger assembly (see, e.g., FIGS. 11A-11B).

In some examples, slots 106-108 and 106a-108a may provide openings in screw 100's shaft to enable material packed inside screw 100 to come into contact with surrounding or adjacent tissue (e.g., bone, cartilage, or other tissue in the joint) when screw 100 is implanted. In some examples, slots 106-108 and 106a-108a may be substantially oval, substantially elliptical, or capsule-shaped (i.e., substantially oval with two parallel sides and two semicircular ends). In other examples, slots 106-108 and 106a-108a may be shaped differently (e.g., circular, rectangular, rounded rectangular, squared or other shapes). In some examples, there may be two or more slots or openings (e.g., slots 106-108) linearly aligned from head 102 to tapered end 120, as shown, along a side of the shaft of screw 100. In some examples, slots 106-108 may be connected to each other and to head 102 and tapered end 120 by linear grooves (e.g., shaft grooves 114a-114c). In some examples, another set of two or more openings (e.g., slots 106a-108a) with connecting shaft grooves (e.g., shaft grooves 116a-116c) may be repeated along another side of the shaft of screw 100. For example, slots 106a-108a and shaft grooves 116a-116c may be disposed linearly from head 102 to tapered end 120 along a side of the shaft of screw 100 approximately ninety degrees (90°) from slots 106-108 and shaft grooves 114a-114c, as shown.

In some examples, tip 104 may be disposed on tapered end 120. In some examples, tip 104 may provide another opening for material packed inside the shaft to come into contact with surrounding or adjacent tissue. In some examples, this opening may be circular, with the same or similar diameter as the cannula of screw 100. In other examples, the opening may be smaller in diameter than the cannula of screw 100 (see FIG. 1C). In some examples, as shown in FIG. 1C, the opening in tip 104 may be contiguous with, and form an end of, screw 100's cannula. In some examples, tapered end 120 may aid in guiding screw 100 into a pilot hole.

In some examples, openings in screw 100, including slots 106-108 and 106a-108a, and tip 104, may enable screw 100 to deliver materials to bone and other joint tissue adjacent to, or surrounding, screw 100, for example, to regenerate bone or treat inflammation, infection, or other ailments, in the joint. For example, screw 100 may have a cannula in which such materials may be packed, as described herein. After being packed, screw 100 may be implanted (i.e., inserted) into or across a joint, and such materials may be delivered from screw 100 through slots 106-108 and 106a-108a, or other openings (e.g., in head 102 or tip 104 of screw 100) and to a joint. In some examples, the above-described materials may enter a joint through slots 106-108 and 106a-108a. In some examples, the above-described materials may fill a joint, partially or entirely, after entering the joint through slots 106-108 and 106a-108a.

In some examples, screws 100 and 200 may be configured to fit or slide within a drill guide (e.g., drill guide 404) and over a guide pin (e.g., guide pin 418) for implantation (e.g., according to processes 1200 and 1300). In other examples, screws 100 and 200 may be formed differently and are not limited to the examples described.

Figure 2A:
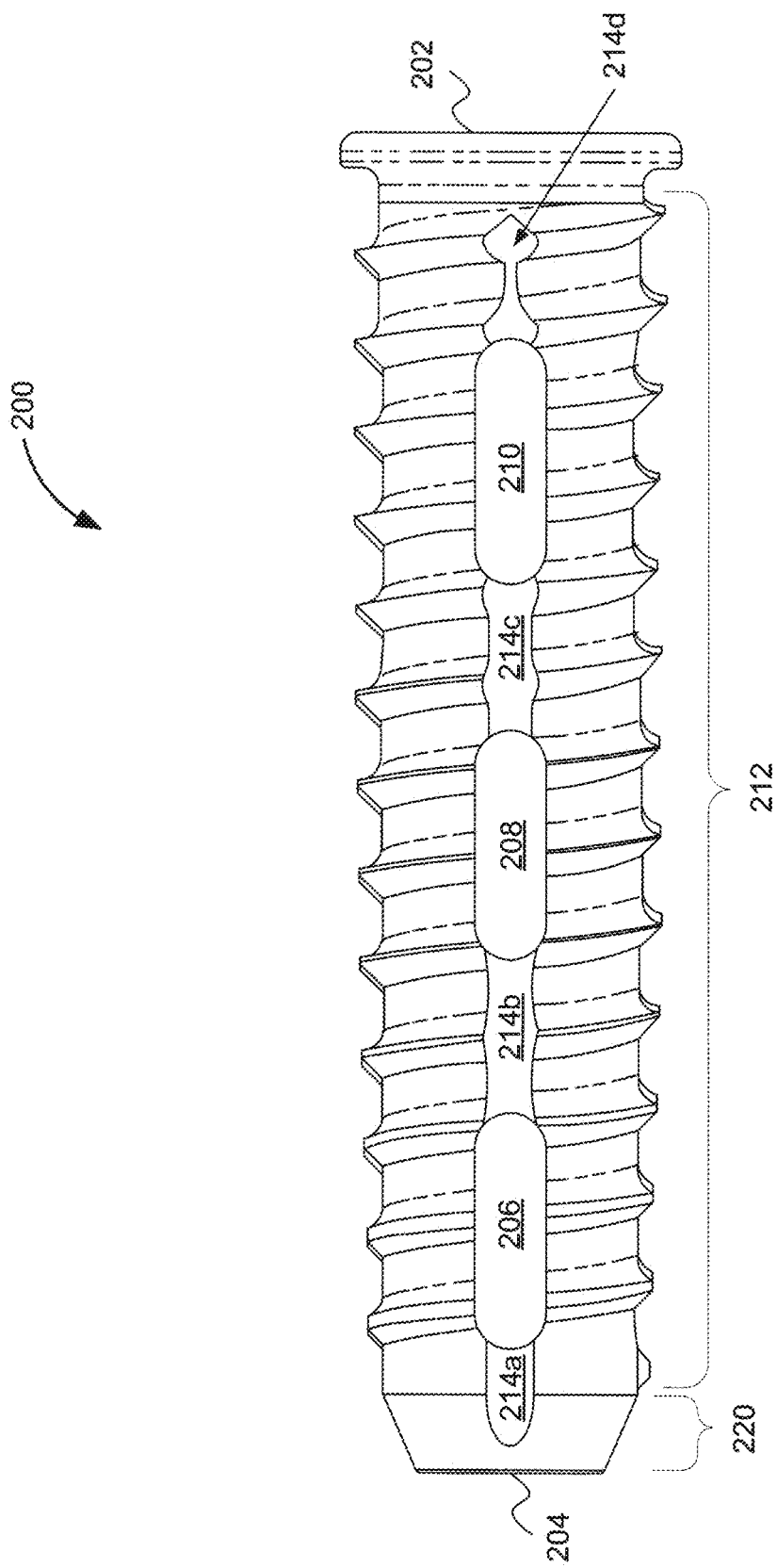
FIGS. 2A-2B illustrate a side view and a perspective view, respectively, of an alternative exemplary screw for joint fusion.
Figure 2B:
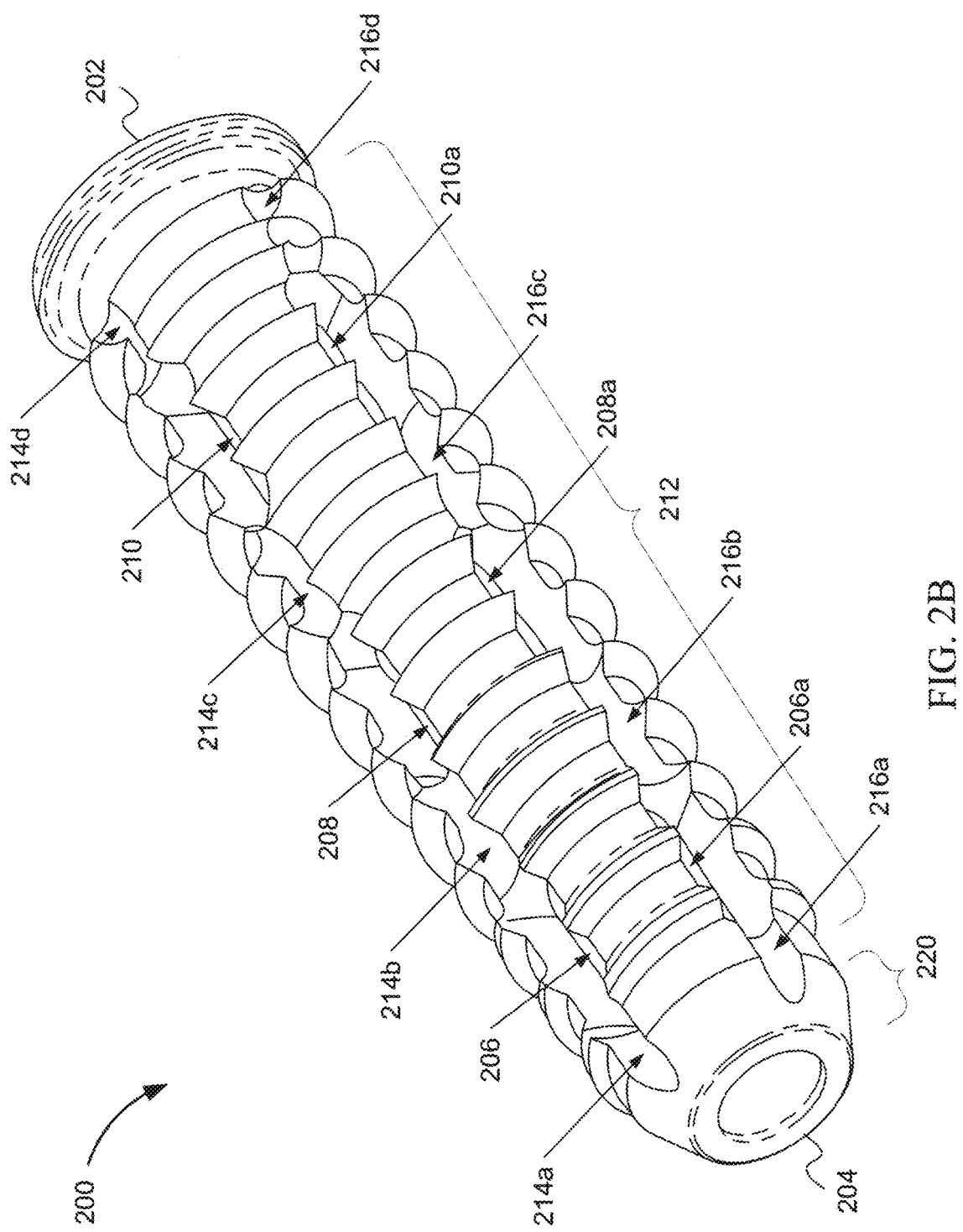

FIGS. 2A-2B illustrate a side view and a perspective view, respectively, of an alternative exemplary screw for joint fusion. Here, screw 200 includes head 202, tip 204, slots 206-210 and 206a-210a, threads 212, shaft grooves 214a-214d and 216a-216d, and tapered end 220 Like-numbered and named elements in these views may describe the same or substantially similar elements above. For example, like-named elements in FIGS. 2A-2B may describe the same or substantially similar elements in FIGS. 1A-1C. In some examples, screw 200 may include three slots (e.g., slots 206-210 or 206a-210a) disposed linearly (i.e., in a line from head 202 to tapered end 220) along one or more sides of screw 200. For example, slots 206-210 may be disposed linearly along one side of screw 200, and slots 206a-210a may be disposed linearly along another side approximately ninety degrees (90°) from slots 206-210.

In some examples, openings in screw 200, including slots 206-210 and 206a-210a, and tip 204, may enable screw 200 to deliver materials to bone and other joint tissue adjacent to, or surrounding, screw 200, for example, to regenerate bone or treat inflammation, infection, or other ailments, in the joint. For example, screw 200 may have a cannula in which such materials may be packed, as described herein. After being packed, screw 200 may be implanted (i.e., inserted) into or across a joint, and such materials may be delivered from screw 200 through slots 206-210 and 206a-210a, or other openings (e.g., in head 202 or tip 204 of screw 100) and to a joint. In some examples, the above-described materials may enter a joint through slots 206-210 and 206a-210a. In some examples, the above-described materials may fill a joint, partially or entirely, after entering the joint through slots 206-210 and 206a-210a.

Figure 3A:
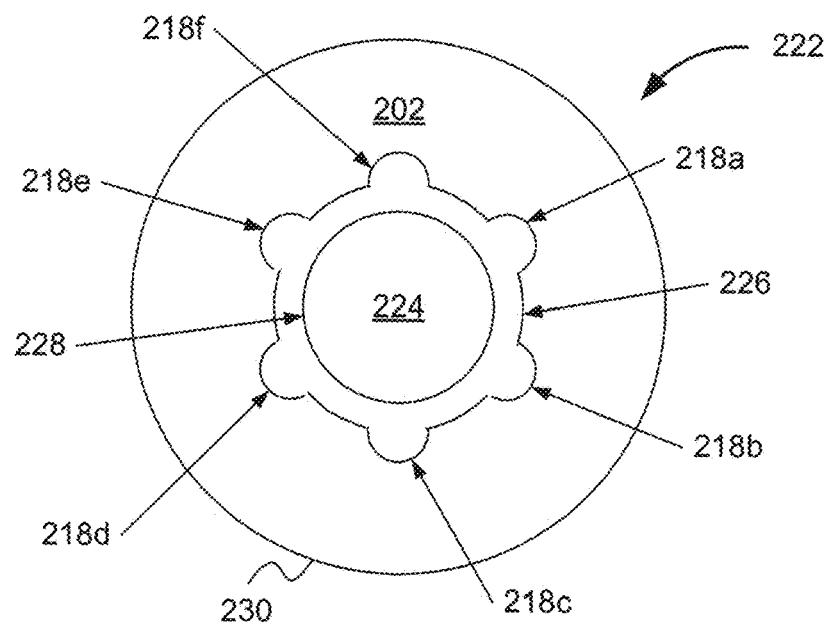
FIG. 3A illustrates a top view of an exemplary screw for joint fusion.

FIG. 3A illustrates a top view of an exemplary screw for joint fusion. Here, top view 222 includes head 202, shaft 224, openings 226-228, head grooves 218a-218f and head diameter 230 Like-numbered and named elements in these views may describe the same or substantially similar elements above. For example, like-named elements in FIG. 3A may describe the same or substantially similar elements in FIGS. 1A-1C & FIGS. 2A-2B. In some examples, head 202 may be circular with head diameter 230. In some examples, head diameter 230 may correspond to the diameter of a cannula of a drill guide (e.g., drill guide 404). In other examples, head 202 may be shaped differently (e.g., triangular, hexagonal, or other shapes not shown). In some examples, opening 226 may be disposed at head 202, and opening 228 may be disposed at tip 204 (see, e.g., FIGS. 2A-2B and 3B). In some examples, the diameters of openings 226 and 228 may be the same or similar. In other examples, the diameter of openings 226 may be different from the diameter of opening 228. In some examples, opening 226 may include head grooves 218a-218f to accept corresponding lobes of a TORX® or TORX®-like driver (i.e., having six lobes). As shown, head grooves 218a-218f may be semi-circular in shape. In other examples, head grooves 218a-218f may be shaped differently (e.g., with points, edges, or other shapes). In other examples, opening 228 may be configured to accept a different type of driver. For example, opening 228 may include more or fewer head grooves that may be shaped the same or differently.

Figure 3B:
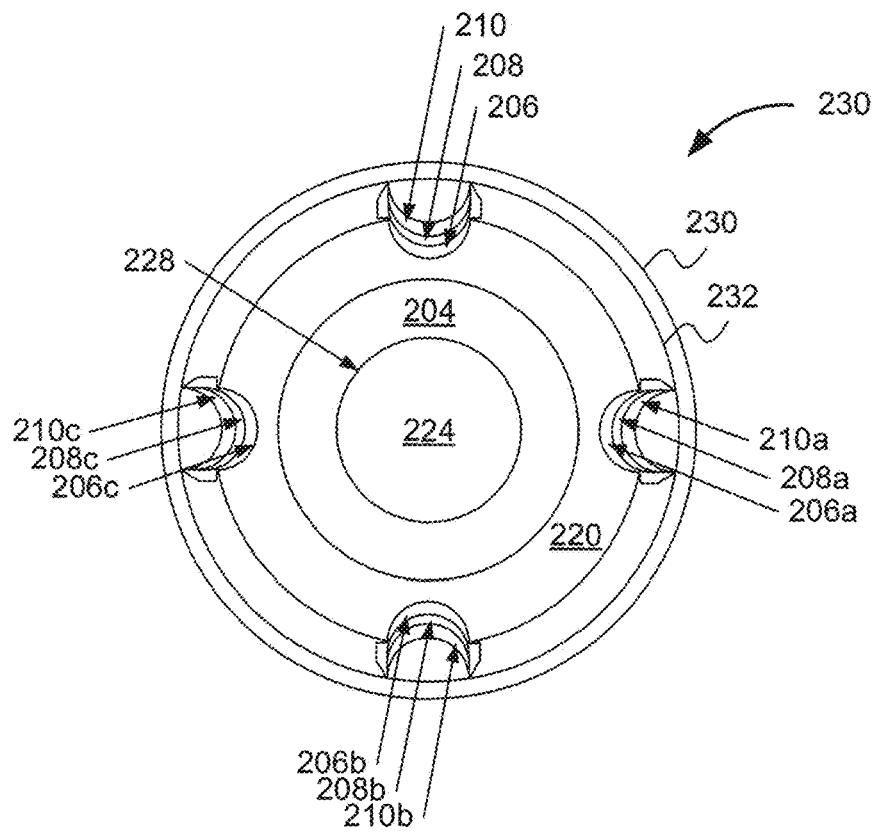
FIG. 3B illustrates a bottom view of an exemplary screw for joint fusion.

In some examples, cannula 224 may extend uninterrupted from head 202 to tip 204 (see FIGS. 2A-2B and 3B). In some examples, cannula 224 may be configured to fit over a guide pin, as described herein. In some examples, cannula 224 also may be configured to receive and hold material (e.g., osteogenic compounds, osteoconductive materials, antibiotics, steroids, contrast materials, or other materials that may beneficial to fusing the joint, treating inflammation or other conditions in the joint, or enabling the visualization of the area within and adjacent to the screw, as described herein).

FIG. 3B illustrates a bottom view of an exemplary screw for joint fusion. Here, bottom view 230 includes tip 204, slots 206-210, 206a-210a, 206b-210b and 206c-210c, tapered end 220, cannula 224, opening 228, head diameter 230 and major diameter 232. Like-numbered and named elements in these views may describe the same or substantially similar elements above. For example, like-named elements in FIG. 3B may describe the same or substantially similar elements in FIGS. 1A-1C, FIGS. 2A-2B and FIG. 3A. In some examples, opening 228 may be disposed at tip 204 and the end of cannula 224. In some examples, head diameter 230 may be larger than major diameter 232, and major diameter 232 in turn may be larger than a minor (i.e., root) diameter (not shown). In some examples, a plurality of slots (e.g., slots 206-210, 206a-210a, 206b-210b and 206c-210c) may be disposed along the walls of cannula 224. In some examples, a first set of three (3) slots (e.g., slots 206-210) may be disposed linearly from head 202 (see FIGS. 2A-2B and 3A) to tip 204 along the wall of cannula 224. In some examples, second, third and fourth sets of slots (e.g., slots 206a-210a, 206b-210b and 206c-210c) may be disposed, also linearly from head 202 to tapered end 220, along the wall of cannula 224 at approximately ninety degree (90°) intervals. In other examples, a screw may have more or fewer sets of linearly disposed slots. In still other examples, each set of linearly disposed slots may include more or fewer slots. In yet other examples, each set of slots may be disposed at greater or lesser intervals.

Figure 4A:
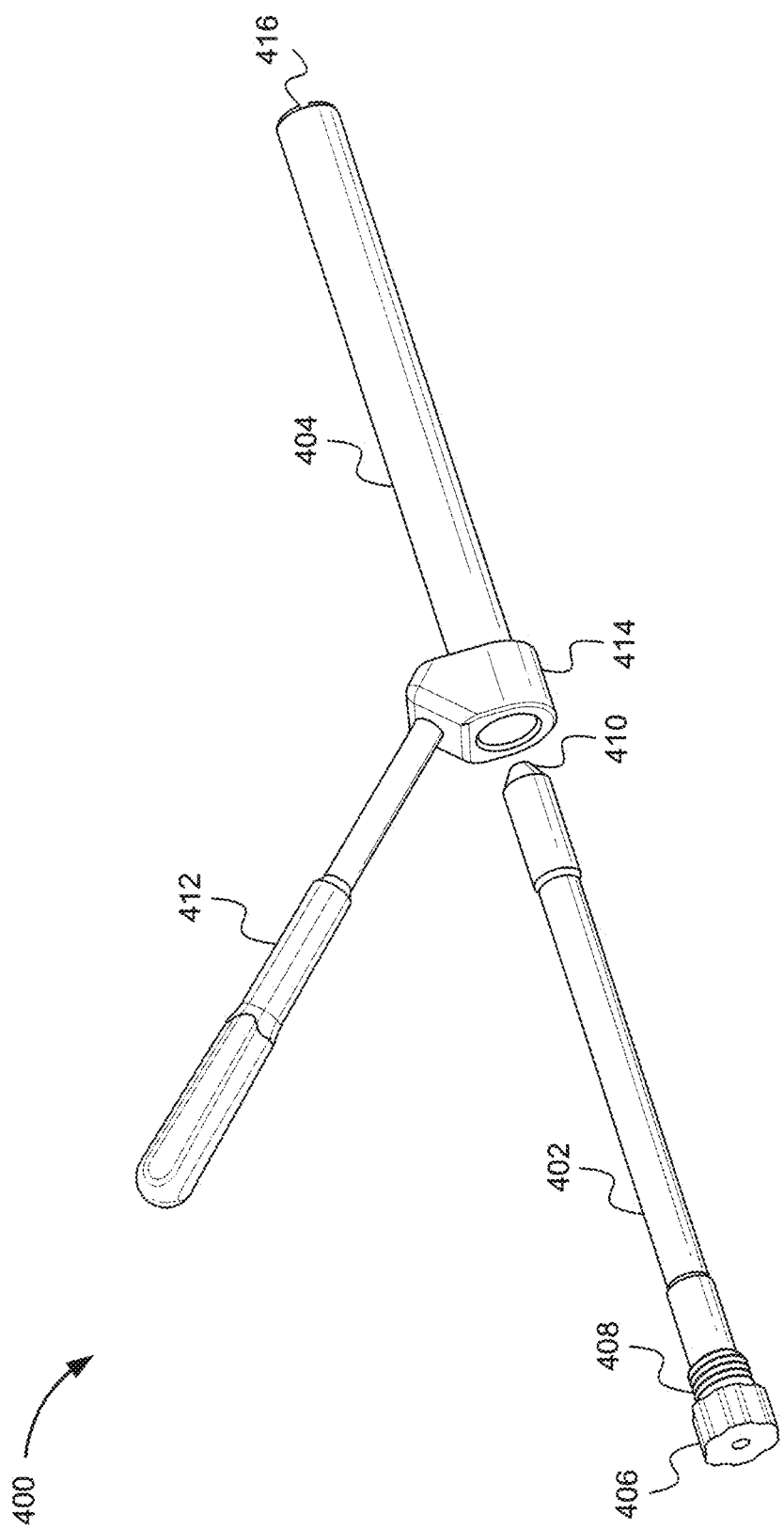
FIG. 4A illustrates an exemplary drill guide assembly having a pin sleeve and a drill guide.

FIG. 4A illustrates an exemplary drill guide assembly having a pin sleeve and a drill guide. Here, drill guide assembly 400 may include pin sleeve 402 and drill guide 404. In some examples, pin sleeve 402 further may include pin sleeve head 406, pin sleeve threads 408, and pin sleeve tip 410. In some examples, drill guide 404 may include handle 412, drill guide head 414, and drill guide tip 416. In some examples, pin sleeve 402 has a hollow shaft that fits more closely over a guide pin than drill guide 404. In some examples, the outer diameter of pin sleeve 402's shaft is shaped to fit inside the cannula of drill guide 404, which has an internal diameter that may be configured to accommodate tools and implants (e.g., screws 100 and 200, and the like) having a larger diameter than a guide pin. For example, the diameter of drill guide 404's cannula may correspond to (i.e., be sized to fit) the head or outer diameter on an implant (e.g., screws 100 and 200). In some examples, the internal surface of drill guide 404 may be configured to guide an implant inserted into drill guide 404 from drill guide head 414 to drill guide tip 416 (e.g., using a groove, an indentation, notch, channel, or the like (not shown) configured to receive a guide point, protrusion, or other structure on an implant (e.g., screws 100 and 200)). In some examples, drill guide head 414 may have threads (not shown) complementary to, and configured to receive, threads 408 on pin sleeve 402. For example, pin sleeve 402 may be inserted into drill guide 404, and they may be screwed together at threads 408 and drill guide head 414 by holding and turning pin sleeve head 406. In some examples, handle 412 may extend from an outer surface of drill guide head 414. In some examples, handle 412 may be used to hold drill guide 404, and other tools and implants that may be coupled to or placed within drill guide 404, in place during an implantation process. In some examples, drill guide tip 416 may have spikes, teeth, wedges, or other structures, to engage a bone. In some examples, guide pin tip 410 may form a trocar for introducing drill guide assembly 400 into a bone.

Figure 4B:
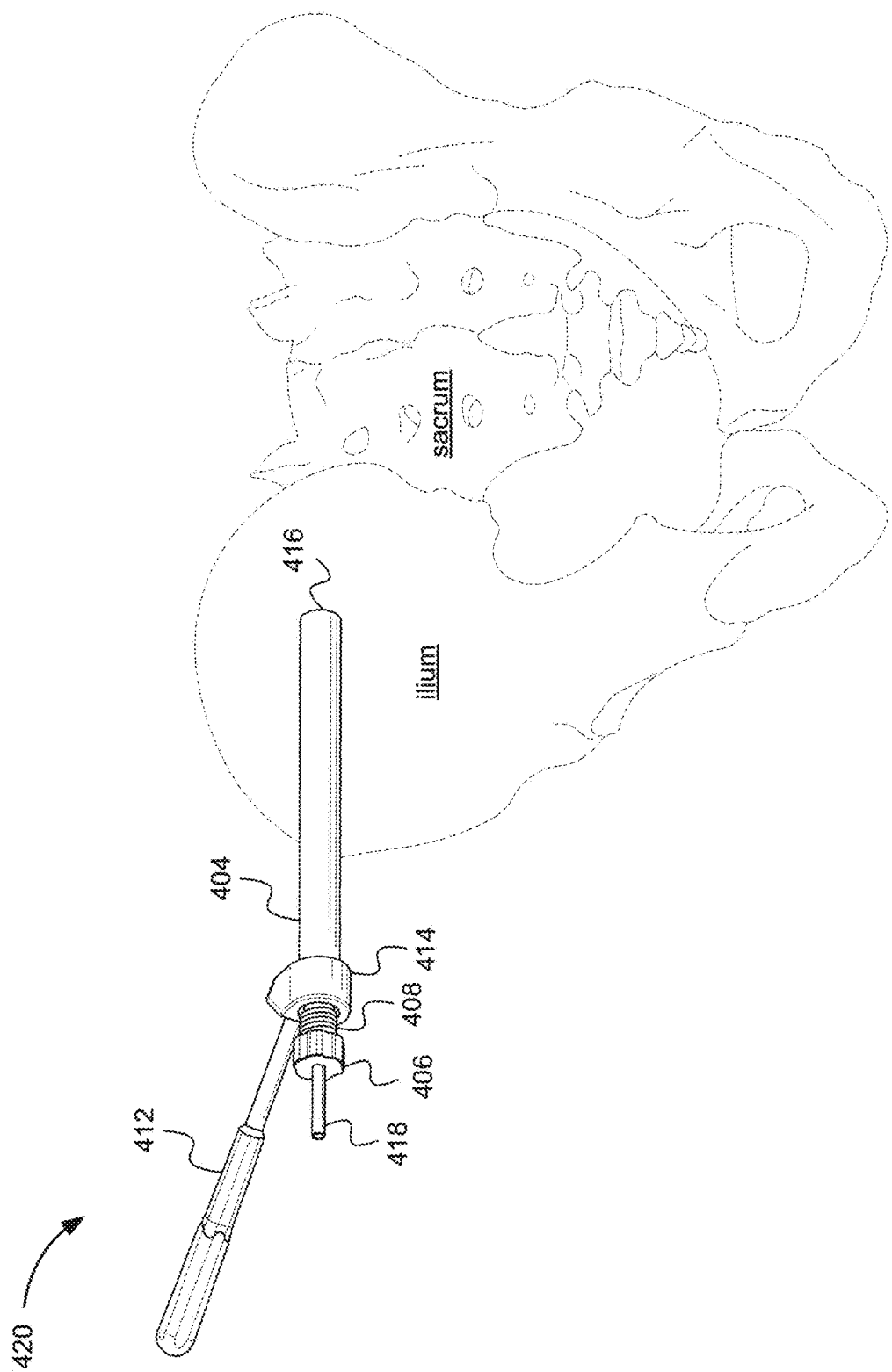
FIG. 4B illustrates an exemplary drill guide assembly placed over a guide pin.

FIG. 4B illustrates an exemplary drill guide assembly placed over a guide pin. Here, diagram 420 may include drill guide 404, pin sleeve head 406 (of pin sleeve 402), threads 408 (of pin sleeve 402), handle 412, drill guide head 414, drill guide tip 416 and guide pin 418. Like-numbered and named elements in this view may describe the same or substantially similar elements as in previous views (e.g., FIG. 4A). In some examples, guide pin 418 may be a medical grade sterile metal pin (e.g., Kirschner wire, Steinmann pin, or other metal pin) suitable for use in medical procedures. In some examples, guide pin 418 may be used for alignment and guidance of a drill guide (e.g., drill guide 404), an implant (e.g., a screw or other implant), and other tools. As shown, drill guide tip 416 is engaged with an ilium (i.e., its spikes, teeth, wedges or other structure for engaging a bone, are embedded in the ilium). In other examples, drill guide assembly 400 may be formed differently and is not limited to the examples described.

Figure 5A:
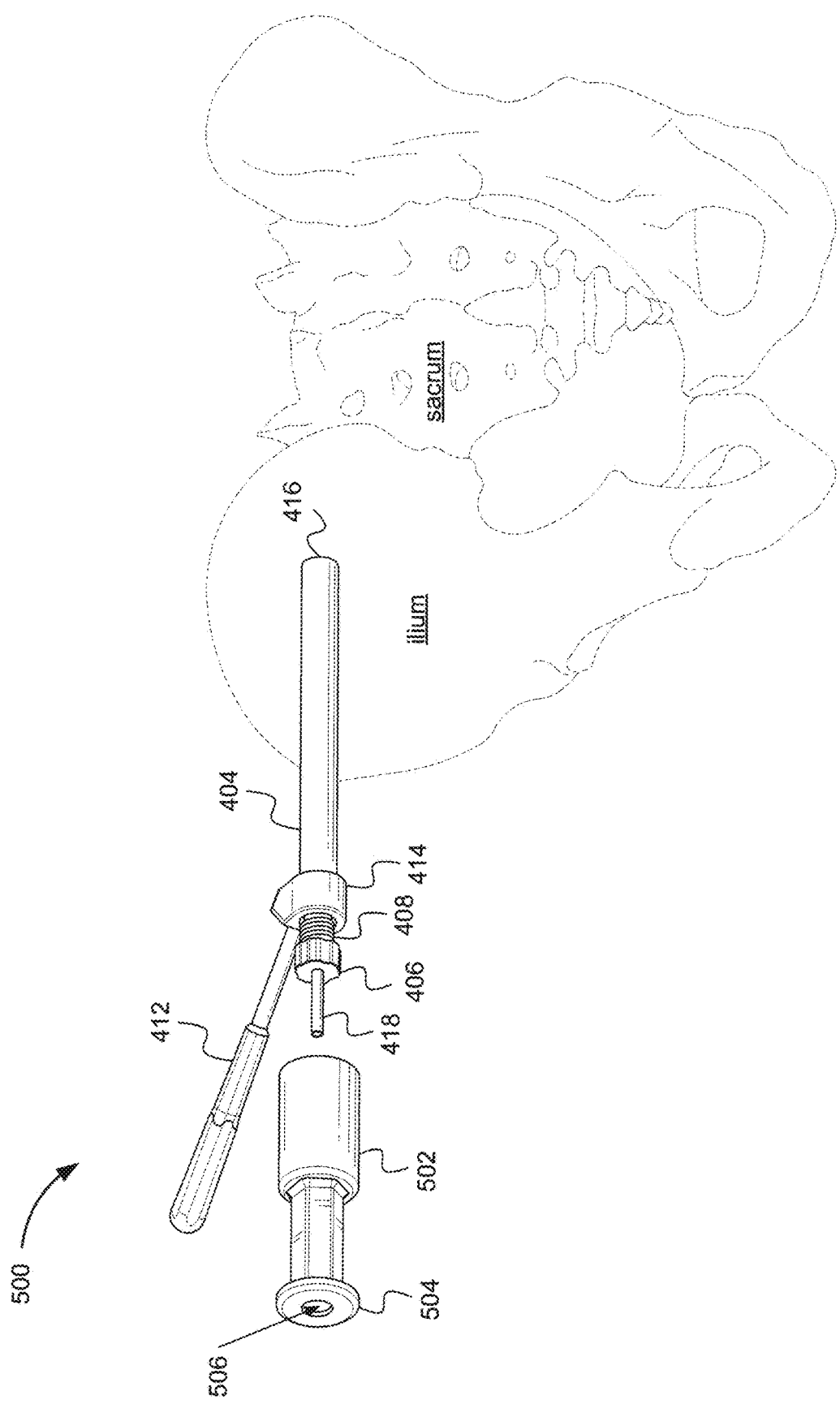
FIGS. 5A-5B illustrate an exemplary striker tube for placement over a drill guide assembly.
Figure 5B:
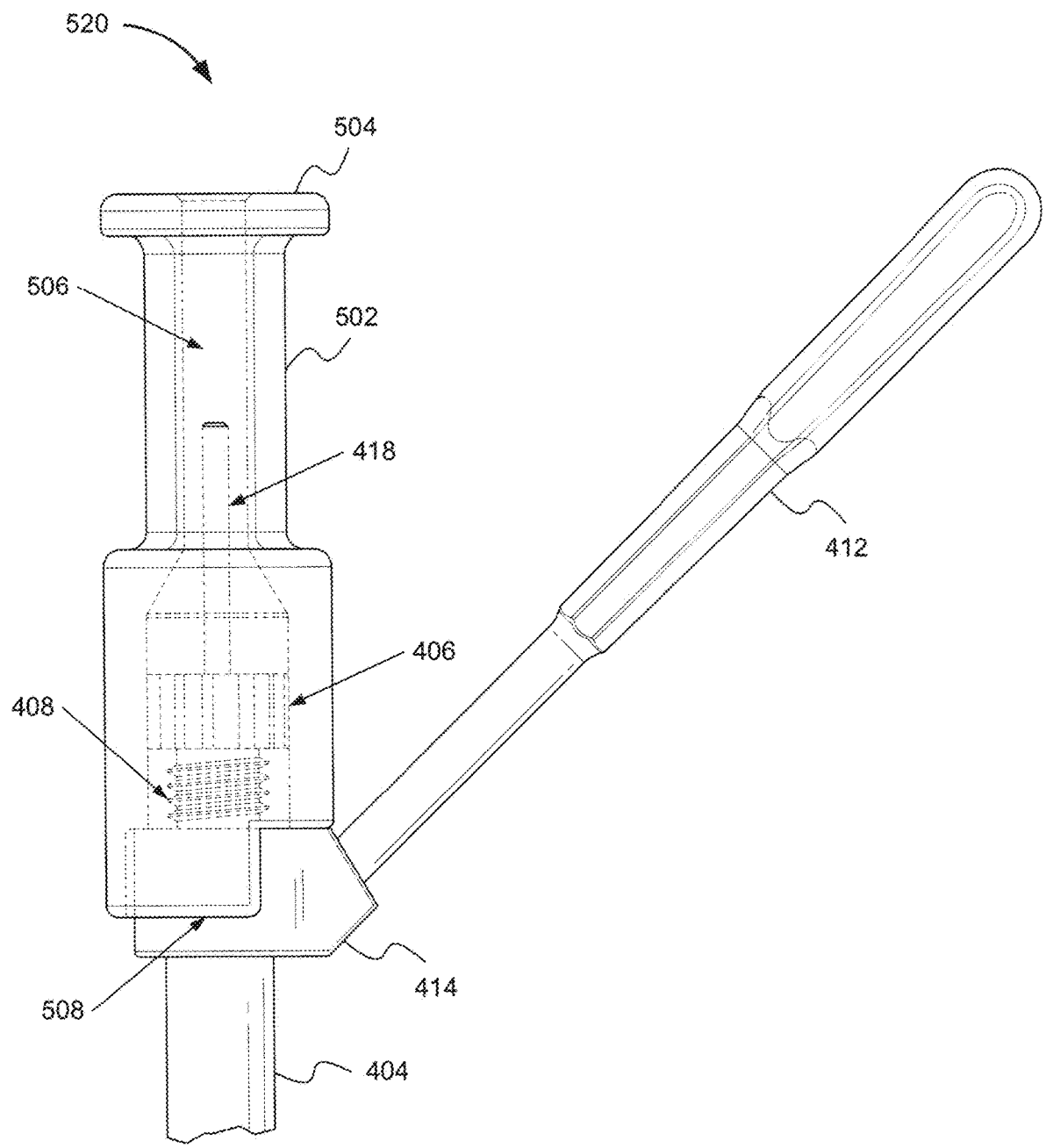

FIGS. 5A-5B illustrate an exemplary striker tube for placement over a drill guide assembly. Here, diagrams 500 and 520 show striker tube 502, striker tube head 504, striker tube cannula 506, edge 508, drill guide 404, pin sleeve head 406, threads 408, handle 412, drill guide head 414, drill guide tip 416 and guide pin 418. Like-numbered and named elements in this view may describe the same or substantially similar elements as in previous views (e.g., FIGS. 4A-4B). In some examples, striker tube 502 may include striker tube head 504, striker tube cannula 506 and edge 508. In some examples, striker tube head 504 may have a flat surface, and may be configured to receive strikes from a flat surface of a mallet. In some examples, striker tube cannula 506 may be shaped to fit over the portions of guide pin 418, pin sleeve head 406 and threads 408 that protrude from drill guide head 414. In some examples, edge 508 may be shaped to fit over drill guide head 414. In some examples, striker tube 502 may push drill guide 404 when stricken with a mallet, causing drill guide 404 to engage a bone. In other examples, striker tube 502 may be formed differently and is not limited to the examples described.

Figure 6:
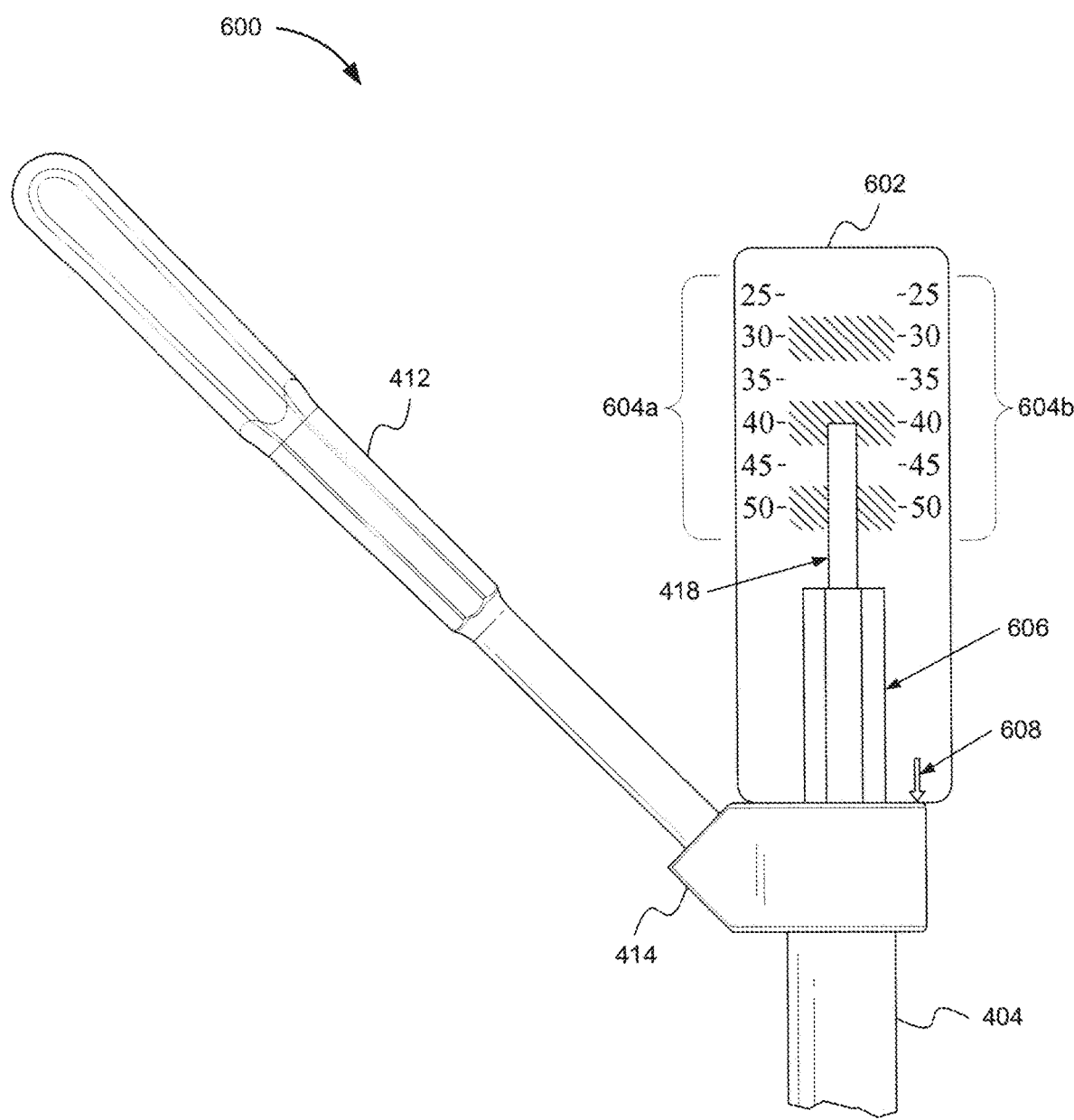
FIG. 6 illustrates an exemplary depth gauge for determining the depth of a pilot hole to be drilled for insertion of a screw for joint fusion.

FIG. 6 illustrates an exemplary depth gauge for determining the depth of a pilot hole to be drilled for insertion of a screw for joint fusion. Here, diagram 600 includes depth gauge 602, depth markings 604a-604b, guide pin receiving element 606, drill guide contact marking 608, drill guide 404, handle 412, drill guide head 414, and guide pin 418. Like-numbered and named elements in this view may describe the same or substantially similar elements as in previous views (e.g., FIGS. 4A-4B & 5A-5B). In some examples, depth gauge 602 may be configured to determine the depth in which guide pin 418 is inserted into a bone and/or joint. In some examples, drill guide contact marking 608 may indicate the edge or side of depth gauge 602 that is to be placed onto drill guide 404 (i.e., at drill guide head 414). In some examples, depth gauge 602 may include depth markings 604a-604b, which account for the lengths of drill guide 404 and guide pin 418, such that when depth gauge 602 is placed over guide pin 418 until drill guide contact marking 608 contacts (i.e., rests against) drill guide head 414, the depth markings 604a-604b may indicate the depth that guide pin 418 has been inserted into a bone or joint. For example, where guide pin 418 is approximately 229 mm long, and drill guide 404 is approximately 140 mm from head 414 to tip 416 (shown in FIGS. 4A-5A), the marking for a 40 mm depth of guide pin 418 may be approximately 48 mm from the edge indicated by drill guide contact marking 608.

In some examples, depth gauge 602 includes guide pin receiving element 606, which is configured to slide over guide pin 418. In some examples, depth markings 604a-604b comprise a set of markings and numbers indicating a range of depths of guide pin 418. In some examples, depth markings 604a-604b may indicate a range of 25-50 mm depths. In other examples, depth gauge 602 may have different depth markings, and thus indicate a different range of depths. In an example, guide pin receiving element 606 may slide over guide pin 418 until drill guide contact marking 608 comes into contact with drill guide head 414. The number in depth markings 604a-604b that corresponds to the location of the end of guide pin 418 may indicate the depth of guide pin 418. In other examples, depth markings 604a-604b may indicate a different depth that may correspond and be calibrated to the depth of guide pin 418 (e.g., depth markings 604a-604b may indicate a desired drilling depth for a pilot hole, a depth of a screw to be implanted, or other depth that is associated with the depth of guide pin 418, and may thus be measured against the depth of guide pin 418). In still other examples, depth gauge 602 may include more or fewer elements and is not limited to the examples described.

Figure 7A:
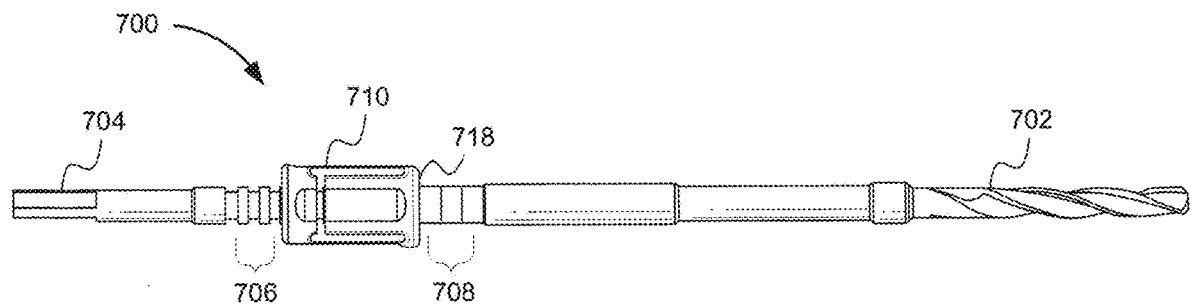
FIG. 7A illustrates a side view of an exemplary cannulated drill bit and stop collar for drilling a pilot hole for insertion of a screw for joint fusion.

FIG. 7A illustrates a side view of an exemplary cannulated drill bit and stop collar for drilling a pilot hole for insertion of a screw for joint fusion. Here, cannulated drill bit 700 may include cutting tip 702, shank 704, adjustment ridges 706, depth markings 708, and may be fitted with stop collar 710, which includes stop collar edge 718. As used herein, "drill bit" refers to any cutting tool configured to create cylindrical holes, and "shank" refers to an end of the drill bit, usually the end opposite the cutting tip, configured to be grasped by a chuck of a drill. In some examples, cannulated drill bit 700 may be configured to drill a pilot hole to a predetermined depth. For example, cutting tip 702 may be configured to cut cylindrical holes into a bone and/or joint when torque and axial force is applied to rotate cutting tip 702 (i.e., by a drill). In some examples, cannulated drill bit 700 may be adjustable, and thereby configured to drill a range of depths using depth markings 708 and the placement of stop collar 710 over adjustment ridges 706 to configure cannulated drill bit 700 to stop drilling at a desired drilling depth. In some examples, stop collar 710 may stop cannulated drill bit 700 from continuing to drill when stop collar edge 718 meets a drill guide head (e.g., drill guide head 414). In this example, the outside diameter of cannulated drill bit 700 may be configured to fit within a drill guide (e.g., drill guide 404), whereas the outside diameter of stop collar edge 718 is larger than the diameter of a drill guide's cannula, and thus stop collar 710 may not fit within a drill guide.

In some examples, a desired drilling depth (i.e., depth of a pilot hole) may be the same or similar to the depth of a guide pin that has been inserted into a bone and/or joint. In other examples, the desired drilling depth may be offset (i.e., less deep) by a predetermined amount (e.g., a few millimeters or other offset amount). For example, if a guide pin has been inserted 40 mm deep into the sacroiliac joint, a corresponding desired drilling depth for the pilot hole may be 40 mm, or it may be 40 mm minus the predetermined offset may be selected (i.e., if the predetermined offset is 3 mm, then the desired drilling depth in this example would be 37 mm) (see FIG. 8).

In some examples, cannulated drill bit 700 may be configured for use with depth gauge 602, and depth markings 708 may correspond to depth markings 604a-604b. For example, if depth gauge 602 has been used to determine that a guide pin (i.e., guide pin 418) has been inserted 40 mm deep into a bone and/or joint, depth markings 708 may include a "40 mm" mark that corresponds to the 40 mm marking on depth gauge 602, wherein the fitting of stop collar 710 onto cannulated drill bit 700 and at the 40 mm marking on cannulated drill bit 700 may guide cannulated drill bit 700 to drill up to, and not beyond, a desired drilling depth corresponding to the 40 mm depth of the guide pin. In this example, if the desired drilling depth is to be the same as the depth of the guide pin, then fitting stop collar 710 onto cannulated drill bit 700 and at the 40 mm marking on cannulated drill bit 700 may stop cannulated drill bit 700 (i.e., when stop collar edge 718 meets drill guide head 414 (not shown)) when the pilot hole is at 40 mm. In another example, if the desired drilling depth is to be offset from the depth of the guide pin by 3 mm, then fitting stop collar 710 onto cannulated drill bit 700 and at the 40 mm marking on cannulated drill bit 700 may stop cannulated drill bit 700 (i.e., when stop collar edge 718 meets drill guide head 414 (not shown)) when the pilot hole is at 37 mm (see FIG. 8).

Figure 7B:
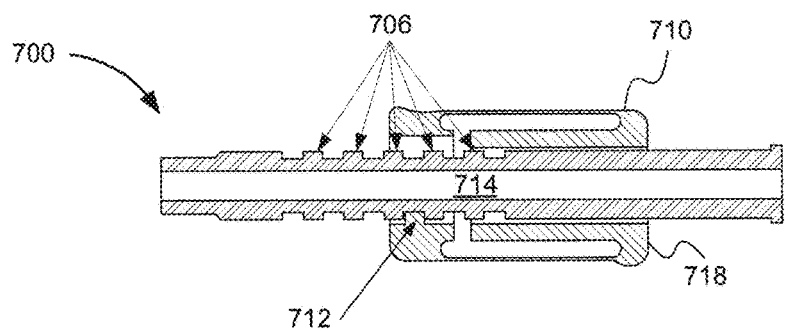
FIG. 7B illustrates a cross-section view of an exemplary cannulated drill bit and stop collar for drilling a pilot hole for insertion of a screw for joint fusion.
Figure 7C:
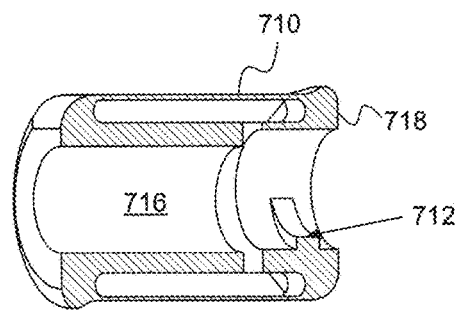
FIG. 7C illustrates a cross-section view of an exemplary stop collar.

FIG. 7B illustrates a cross-section view of an exemplary cannulated drill bit and stop collar for drilling a pilot hole for insertion of a screw for joint fusion. Here, cannulated drill bit 700 includes adjustment ridges 706, cannula 714, and may be fitted with stop collar 710, which may include stop collar ridge 712. In some examples, cannula 714 may be configured (i.e., sized) to fit over a guide pin (e.g., guide pin 418). FIG. 7C illustrates a cross-section view of an exemplary stop collar, which shows stop collar 710, including stop collar ridge 712 and stop collar cannula 716. In some examples, cannulated drill bit 700 may be configured to fit into cannula 716. In some examples, stop collar ridge 712 may engage adjustment ridges 706 when stop collar 710 is placed over cannulated drill bit 700 and twisted or turned. In some examples, stop collar ridge 712 may engage adjustment ridges 706 by sliding in between a set of two of adjustment ridges 706 when stop collar 710 is turned. In other examples, cannulated drill bit 700 and stop collar 710 may be formed differently and are not limited to the examples described.

FIG. 8 illustrates a cross-section view of an exemplary sacroiliac joint with an applied guide pin, drill bit and drill guide. Here, diagram 800 includes drill guide 404, drill guide tip 416, guide pin 418, and cannulated drill bit 700 with cutting tip 702. Like-numbered and named elements in this view may describe the same or substantially similar elements as in previous views (e.g., FIGS. 4A-4B, 5A-5B, 6 & 7A-7C). In some examples, drill guide 404 may engage an ilium using drill guide tip 416, as described herein. In some examples, drill guide 404 may comprise a cannula or hollow shaft configured to fit over various tools for use in inserting an implant into a bone and/or joint (e.g., pin sleeve 402, cannulated drill bit 700, driver 902, packing tube 1102, or other tools), which may in turn be configured to fit over (i.e., slide onto) a guide pin. For example, cannulated drill bit 700 may be configured to fit or slide into drill guide 404 and over guide pin 418. In some examples, cannulated drill bit 700 may be configured to drill a pilot hole depth that is offset from the depth of the guide pin (e.g., guide pin 418) by a predetermined distance, such that cutting tip 702 may stop a predetermined distance before reaching the end of guide pin 418.

Figure 9:
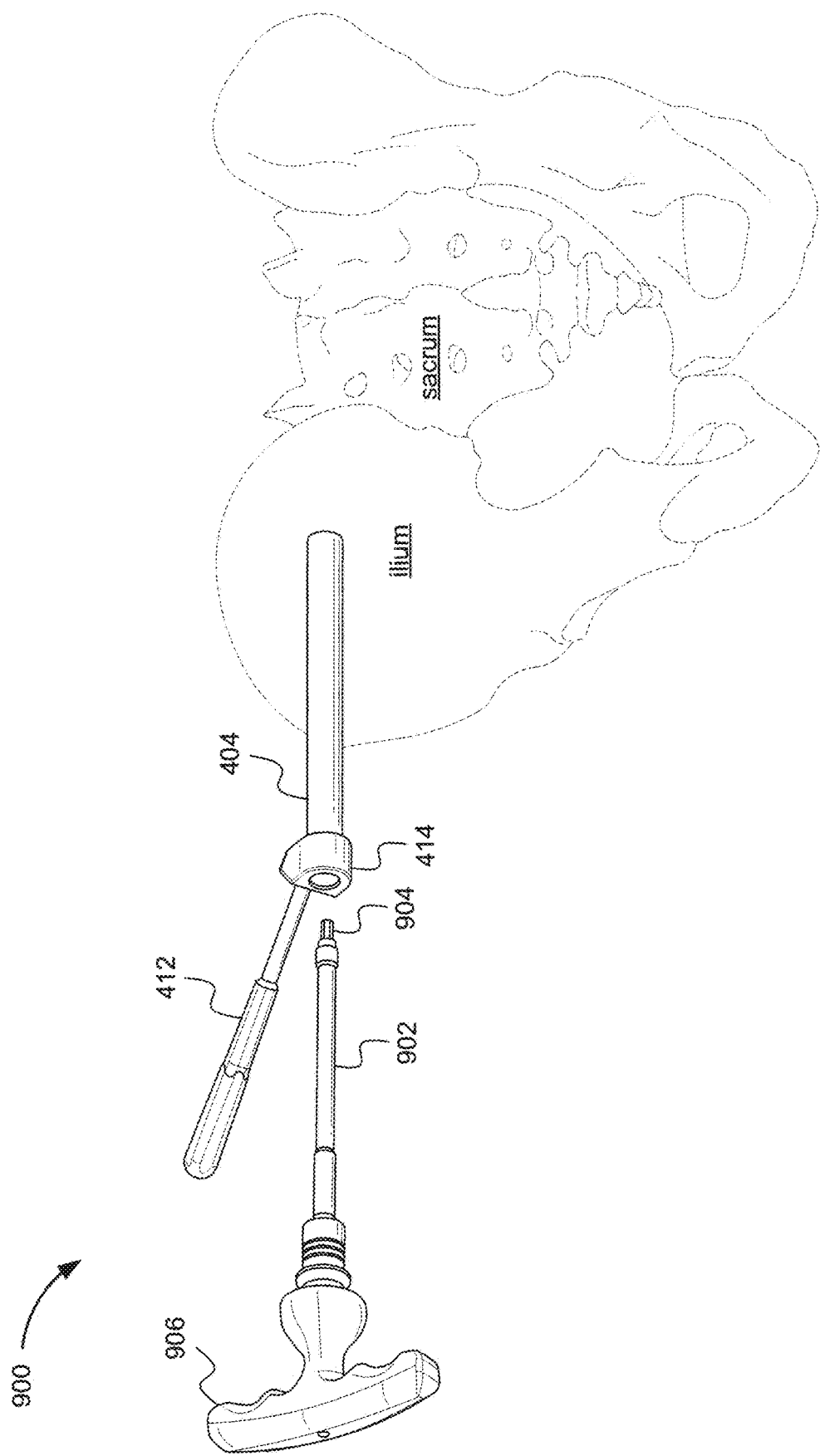
FIG. 9 illustrates an exemplary driver for inserting a screw for joint fusion.

FIG. 9 illustrates an exemplary driver for inserting a screw for joint fusion. Here, diagram 900 includes driver 902, mating tip 904, driver handle 906, drill guide 404, handle 412, and drill guide head 414 Like-numbered and named elements in this view may describe the same or substantially similar elements as in previous views (e.g., FIGS. 4A-4B, 5A-5B, 6, 7A-7C & 8). In some examples, driver 902 may be configured to drive a screw (e.g., screws 100 and 200) into a bone and/or joint. In some examples, driver 902 may have a shaft configured to fit or slide within drill guide 404. In some examples, mating tip 904 may be shaped to engage (i.e., fit) a head of a screw (e.g., heads 102 and 202). For example, driver 902 may be a TORX® driver and mating tip 904 may be shaped to fit a TORX® head screw (e.g., with a six-point or six-lobed shape). In other examples, mating tip 904 may be shaped differently to engage different types of screws (e.g., PHILLIPS™ (i.e., having a cruciform or cross shape with four lobes), slot, flat, Robertson, hex, or other type of screws). In some examples, driver handle 906 may be used to turn driver 902, and consequently turn a screw engaged by mating tip 904. In some examples, driver 902 may be a manual driver. In other examples, driver 902 may be powered (i.e., electrically). In some examples, driver 902 also may be ratcheting or torque-limited. In some examples, driver handle 906 may be formed separately from driver 902's shaft and driver tip 904. In some examples, handle 906 may be configured to be removably coupled with various types of drivers (e.g., TORX®, PHILLIPS™, slot, flat, Robertson, hex, or other types of screwdrivers). In other examples, driver 902 and driver handle 906 may be formed differently, and are not limited to the examples shown and described.

Figures 10A, 10B:
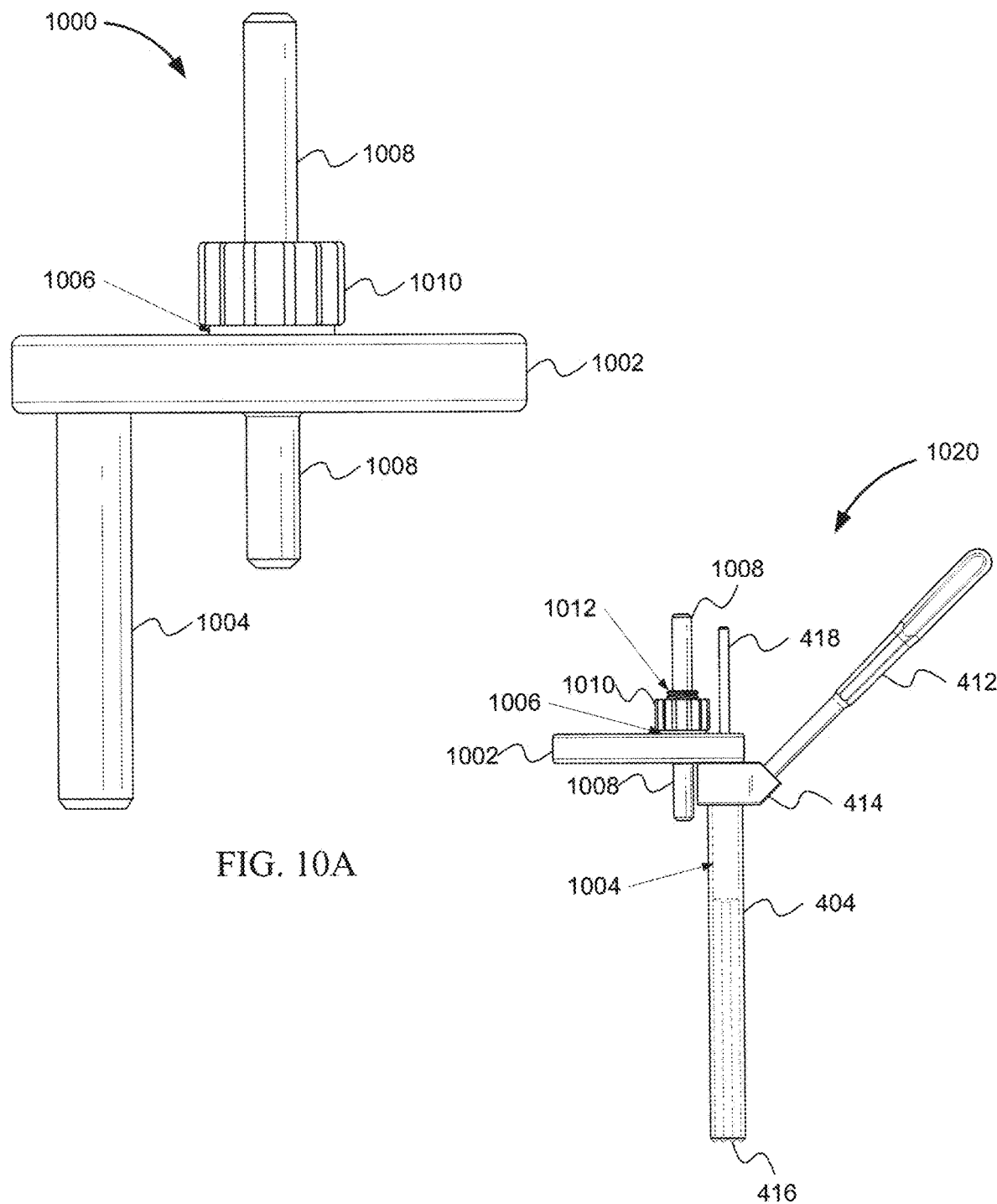
FIG. 10A illustrates a side view of an exemplary parallel spacer instrument for placement of another guide pin.
FIG. 10B illustrates a side view of an exemplary parallel spacer instrument for placement of another guide pin as placed on a drill guide.

FIG. 10A illustrates a side view of an exemplary parallel spacer instrument for placement of another guide pin. Here, parallel spacer instrument 1000 includes parallel spacer block 1002, drill guide tube 1004, sliding block 1006, guide pin tube 1008 and locking nut 1010. Like-numbered and named elements in this view may describe the same or substantially similar elements as in previous views (e.g., FIGS. 4A-4B, 5A-5B, 6, 7A-7C, 8 & 9). In some examples, parallel spacer instrument 1000 may be configured to place another or a next guide pin at a distance from a previously placed implant (i.e., a previously implanted screw). In some examples, drill guide tube 1004 may be integrally formed with parallel spacer block 1002. In some examples, guide pin tube 1008 may be integrally formed with sliding block 1006. In some examples, sliding block 1006 may fit within an opening in, and be adjustably coupled to, parallel spacer block 1002 (see, e.g., FIGS. 10C-10D). For example, sliding block 1006 may be coupled to parallel spacer block 1002 in a manner that enables sliding block 1006 to slide horizontally along an opening in parallel spacer block 1002 (see, e.g., FIGS. 10C-10D). In some examples, locking nut 1010 may be used to secure sliding block 1006 to parallel spacer block 1002.

In some examples, drill guide tube 1004 may be sized (i.e., have an outer diameter configured) to fit within the cannula of a drill guide, and also may have its own hollow shaft (i.e., a drill guide tube cannula) configured to fit around or over a guide pin, as shown in FIG. 10B. FIG. 10B illustrates a side view of an exemplary parallel spacer instrument for placement of another guide pin as placed on a drill guide. Here, diagram 1020 includes, parallel spacer block 2002, drill guide tube 1004, sliding block 1006, guide pin tube 1008, locking nut 1010, threads 1012, drill guide 404, handle 412, drill guide head 414, drill guide tip 416 and guide pin 418. Like-numbered and named elements in this view may describe the same or substantially similar elements as in previous views (e.g., FIGS. 4A-4B, 5A-5B, 6, 7A-7C, 8, 9 & 10A). As shown, drill guide tube 1004 may fit into drill guide 404, with part of parallel spacer block resting against drill guide head 414. Also as shown, drill guide tip 416 may have spikes, teeth, wedges, or other structures configured to assist drill guide 404 with engaging a bone. In some examples, guide pin 418 may still be in place within drill guide 404, in which case drill guide tube 1004 may fit over guide pin 418. In some examples, once parallel spacer instrument 1000 is placed on drill guide 404, a next guide pin (not shown) may be inserted through guide pin tube 1008 until the end of the next guide pin rests against a bone (i.e., an ilium). While in place in guide pin tube 1008, the next guide pin may be advanced into the bone and through a joint to a desired depth using a mallet.

Figure 10C:
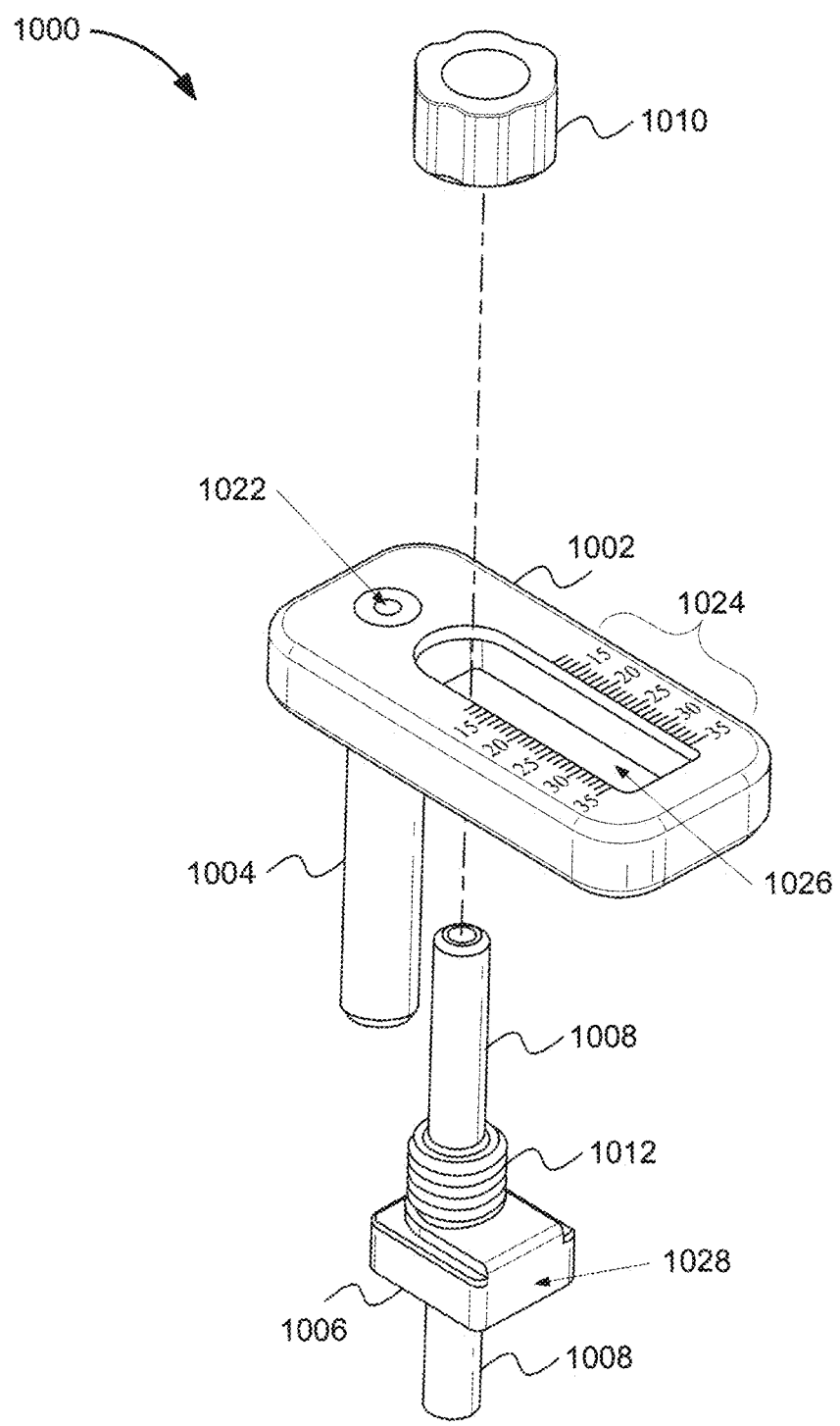
FIG. 10C illustrates an exploded view of an exemplary parallel spacer instrument.
Figure 10D:
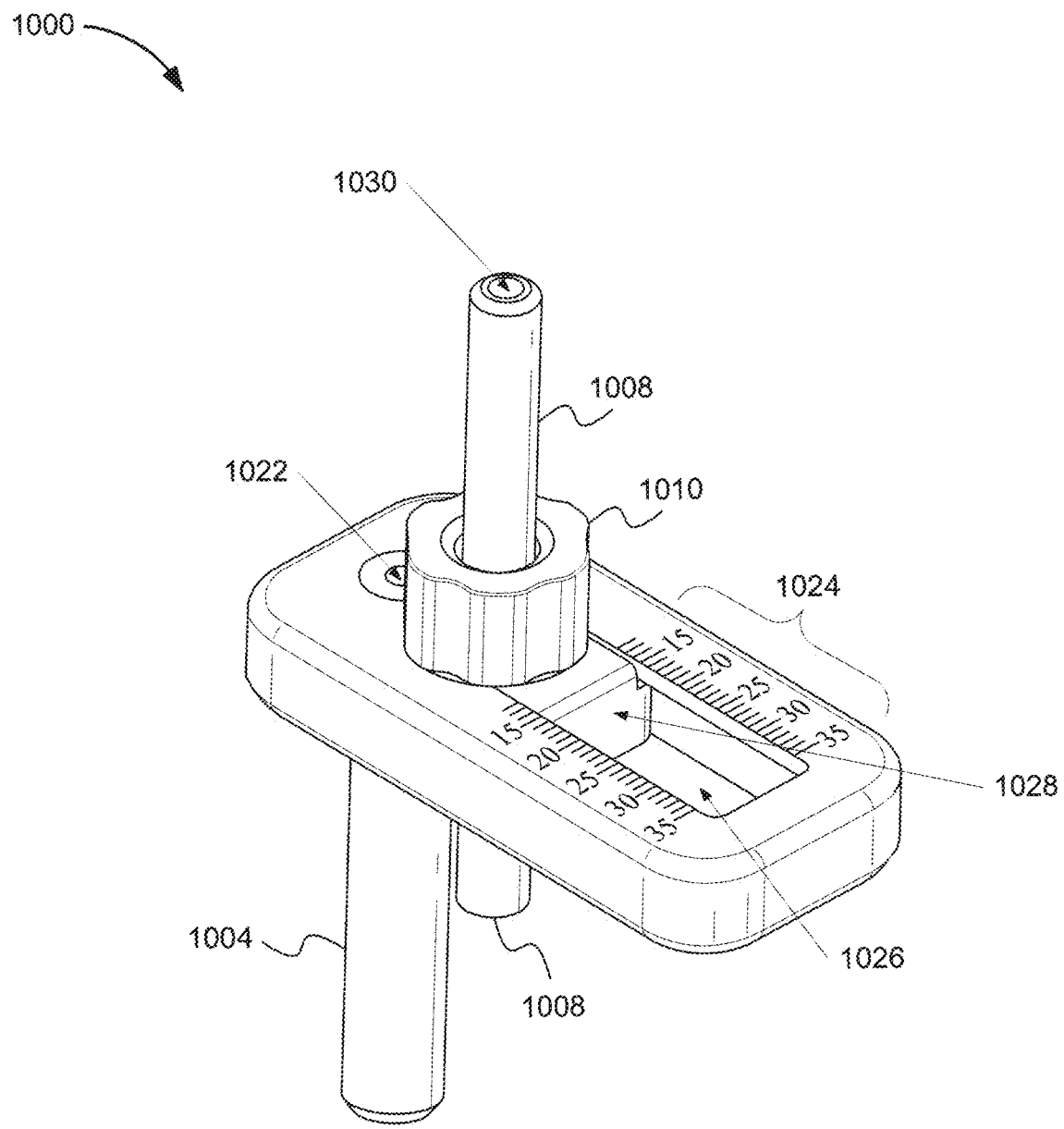
FIG. 10D illustrates a perspective view of an exemplary parallel spacer instrument.

FIG. 10C illustrates an exploded view of an exemplary parallel spacer instrument; and FIG. 10D illustrates a perspective view of an exemplary parallel spacer instrument. Here, parallel spacer instrument 1000 includes parallel spacer block 1002, opening 1026, spacer markings 1024, drill guide tube 1004, drill guide tube cannula 1022, sliding block 1006, leading edge 1028, guide pin tube 1008, guide pin tube cannula 1030, locking nut 1010, and threads 1012 Like-numbered and named elements in this view may describe the same or substantially similar elements as in previous views (e.g., FIGS. 4A-4B, 5A-5B, 6, 7A-7C, 8, 9 & 10A-10B). In some examples, parallel spacer block may include opening 1026 for receiving sliding block 1006. Opening 1026 may be sized to allow sliding block 1006 to slide horizontally within parallel spacer block 1002. In some examples, parallel spacer block 1002 may comprise spacer markings 1024 with numerical labels for measuring out the spacing between implants. In some examples, when leading edge 1028 is placed at one of spacer markings 1024, the number corresponding to that marking may indicate the space (i.e., distance, for example, in millimeters) between a previously placed implant, as placed by a drill guide (e.g., drill guide 404) within which drill guide tube 1004 is inserted, and a guide pin placed in guide pin tube 1004 (i.e., the next guide pin). This, in turn, may determine the spacing between an implant and a next implant. In some examples, drill guide tube cannula 1022 and guide pin tube cannula 1030 each may be configured (e.g., have a diameter fit, or be sized) to receive a guide pin. In some examples, guide tube cannula 1022 and guide pin tube cannula 1030 may have the same diameter.

In some examples, sliding block 1006 may slide horizontally within opening 1026 until leading edge 1028 reaches a marking corresponding to a desired spacing for a next implant. Once sliding block 1006 is at the desired setting, locking nut 1010 may be used to tighten or securely couple sliding block 1006 to parallel spacer block 1002 such that sliding block 1006 stops sliding within opening 1026. For example, locking nut 1010 may be tightened by screwing locking nut 1010 onto threads 1012. In some examples, sliding block 1006 may be reset to a different spacing at a later time by unscrewing locking nut 1010 to loosen or release sliding block 1006 from parallel spacer block 1002. In other examples, parallel spacer instrument 1000 may be formed differently and is not limited to the examples shown and described.

Figure 11A:
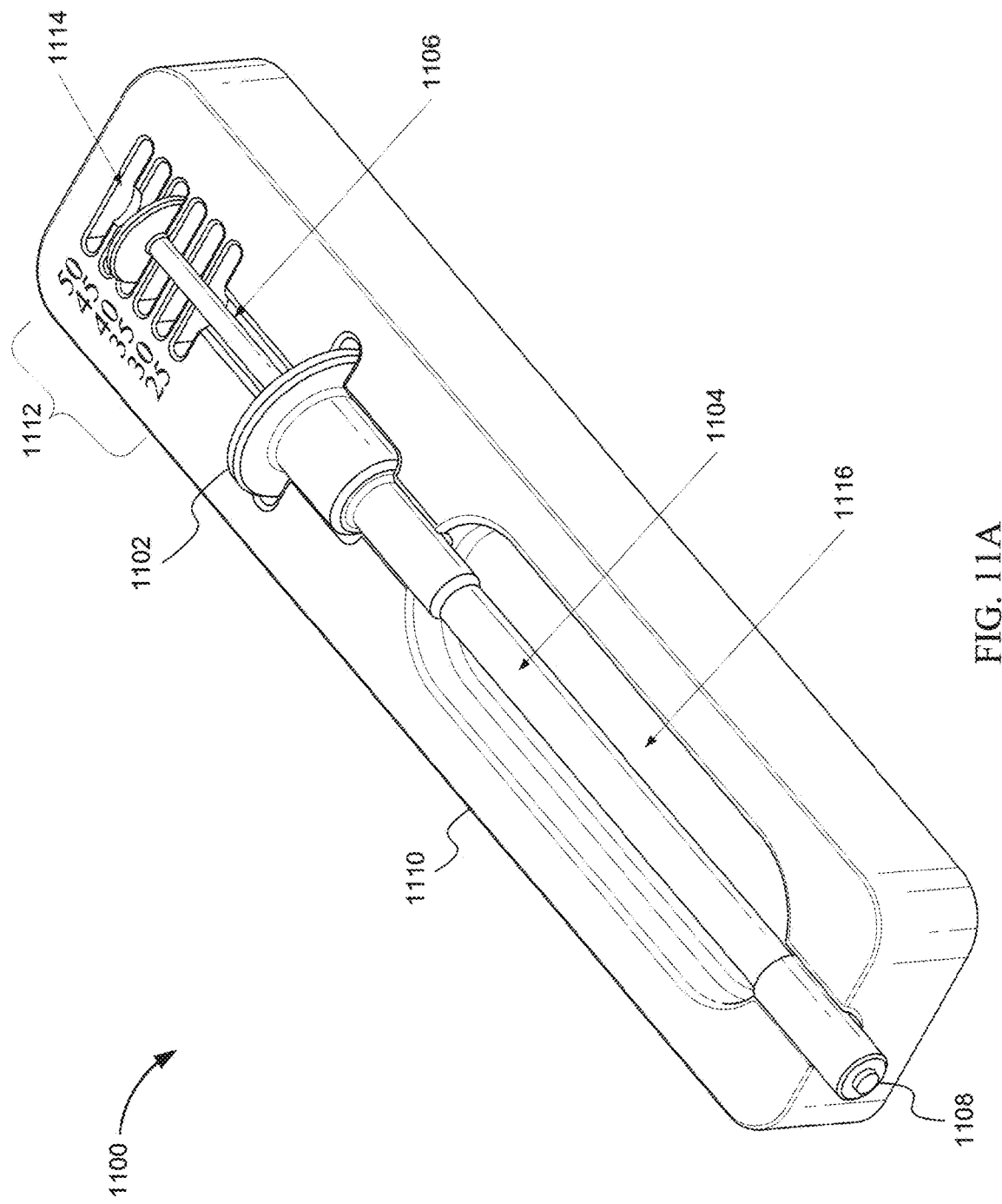
FIG. 11A illustrates a perspective view of an exemplary packing plunger assembly placed in an exemplary plunger distance tool.
Figure 11B:
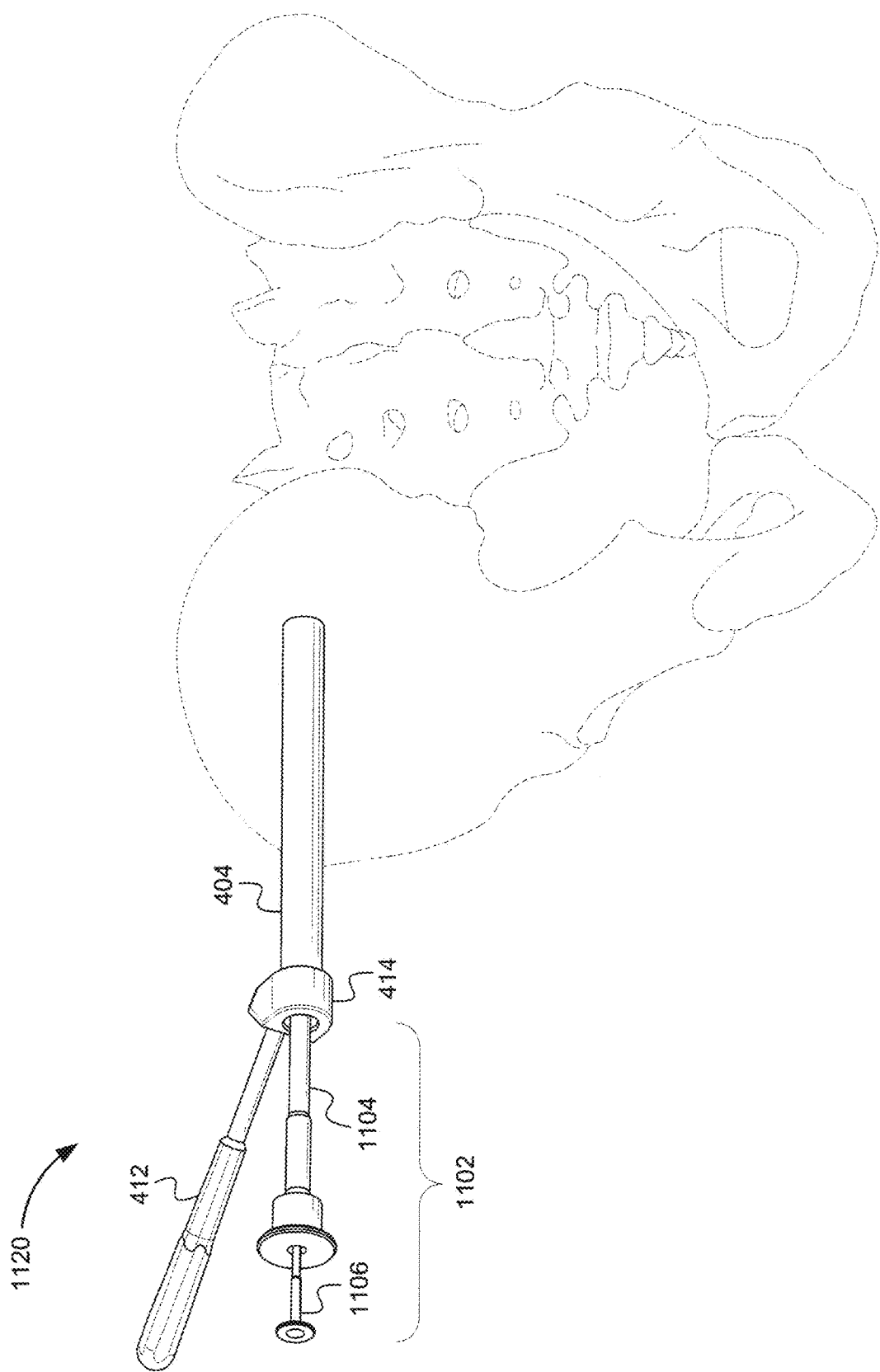
FIG. 11B illustrates an exemplary packing plunger assembly placed in a drill guide for packing a screw for joint fusion.

FIG. 11A illustrates a perspective view of an exemplary packing plunger assembly placed in an exemplary plunger distance tool; and FIG. 11B illustrates an exemplary packing plunger assembly placed in a drill guide for packing a screw for joint fusion. Here, diagrams 1100 and 1120 include packing plunger assembly 1102, packing tube 1104, plunger 1106, loading port 1108, plunger distance tool 1110, plunger distance markings 1112, one or more plunger wells 1114, drill guide 404, handle 412, and drill guide head 414. Like-numbered and named elements in this view may describe the same or substantially similar elements as in previous views (e.g., FIGS. 4A-4B, 5A-5B, 6, 7A-7C, 8 & 9). In some examples, packing plunger assembly 1102 may comprise packing tube 1104, plunger 1106 and loading port 1108. In some examples, packing tube 1104 may be coupled to plunger 1106 with a portion of plunger 1106 inserted into packing tube 1104 to form packing plunger assembly 1102. In some examples, packing tube 1104 and plunger 1106 may be coupled such that plunger 1106 has a plunger shaft configured to be inserted into a hollow internal space (i.e., cannula) inside packing tube 1104, the plunger shaft of plunger 1106 fitting into packing tube 1104 such that pushing (i.e., depressing) plunger 1106 acts to modify the internal volume of packing tube 1104 (e.g., plunger shaft of plunger 1106 has a diameter that fits within packing tube 1104's cannula such that an exterior surface of plunger 1106's shaft contacts an interior surface of packing tube 1104, or plunger 1106 fits within packing tube 1104 such that an exterior surface of plunger 1106 creates a seal with an internal surface of packing tube 1104, or the like). For example, plunger 1106 may be moved in and out of an end of packing tube 1104 to draw into, and dispense out from, packing tube 1104 various materials (e.g., liquids, gases, gels, or other materials, as described herein), for example, through loading port 1108. In some examples, loading port 1108 may be disposed at an end of packing tube 1104, which may be opposite another end of packing tube 1104 in which a plunger shaft of plunger 1106 may be inserted. In some examples, loading port 1108 may comprise an opening between a cannula within packing tube 1104 and an environment outside of packing tube 1104. As described herein, such materials may include osteogenic compounds (e.g., bone morphogenetic protein, or other osteogenic compounds that may ossify tissue in the joint), osteoconductive materials (e.g., demineralized bone, hydroxyappatite, or other material that promotes bone growth), antibiotics, steroids, contrast materials, or other materials that may beneficial to fusing the joint, treating inflammation or other conditions in the joint, or enabling the visualization of the area within and adjacent to the screw. In some examples, packing tube 1104 may be filled with an amount of one or more of these materials to be packed into an implant (e.g., screws 100 and 200), as described herein. In some examples, packing tube 1104 may be filled using loading port 1108 (e.g., material may be drawn into packing tube 1104 through loading port 1108, material may be pushed or otherwise dispensed into packing tube 1104 through loading port 1108, or other loading methods may be employed). In some examples, plunger 1106 may be depressed to dispense material from packing tube 1104 out through loading port 1108, for example, into a cannulated screw (e.g., screws 100 and 200), which may in turn deliver said material into a joint, as described above, through openings (e.g., slots 106-108, 106a-108a, 206-210, and 206a-210a, or the like) disposed on the shaft of said cannulated screw (e.g., screws 100 and 200, or the like), or through other openings (e.g., in head 102, head 202, tip 104 and tip 204, or the like).

In some examples, plunger distance tool 1110 may include bed 1116, plunger distance markings 1112 and corresponding plunger wells 1114. For example, plunger wells 1114 may be shaped to receive the head of plunger 1106. In some examples, plunger distance tool 1110 may be used to determine a position of plunger 1106 corresponding to the size of implant to be packed. For example, as shown in FIG. 11A, when the head of plunger 1106, with plunger 1106 coupled to packing tube 1104 is placed into the one of plunger wells 1114 corresponding to the "40" or 40 mm plunger distance marking and packing tube 1104 is placed onto bed 1116, this sets packing plunger assembly 1102 to have an internal volume be filled with an amount of material appropriate for packing a 40 mm screw, as described herein.

In some examples, loading port 1108 may be configured to fit onto, or engage, the head of a cannulated screw (e.g., screws 100 and 200). For example, loading port 1108 may have an opening disposed on the end of a tubular protrusion sized to fit within an opening in the top of a cannulated screw. Once loading port 1108 is engaged with the head of a cannulated screw, plunger 1106 may be depressed to dispense material from packing tube 1104, out through an opening at an end of loading port 1108, and into a cannulated screw (e.g., screws 100 and 200), which may in turn deliver said material into a joint, as described above.

In some examples, packing plunger assembly 1102 may be used with a drill guide (e.g., drill guide 404) to pack an implanted screw with material, as shown in FIG. 11B. In other examples, packing plunger assembly 1102 may be used without a drill guide to pack a screw, for example, before implantation of the screw. In yet other examples, packing plunger assembly 1102 may be used without a drill guide to pack a previously implanted screw. In still other examples, packing plunger assembly 1102 may be formed differently and is not limited to the examples described.

Figure 12:
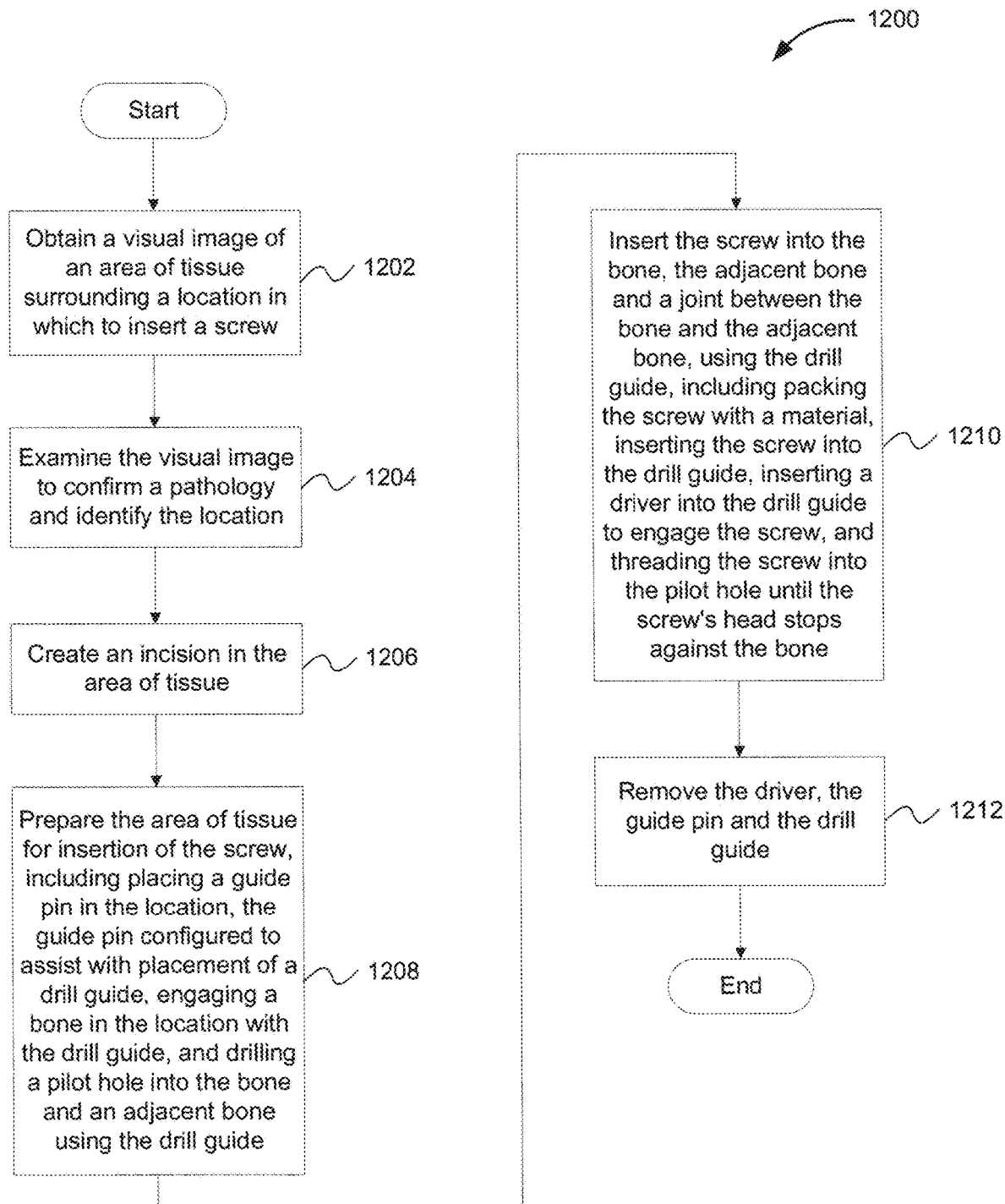
FIG. 12 illustrates an exemplary process for joint fusion.

FIG. 12 illustrates an exemplary process for joint fusion. Here, process 1200 begins with obtaining a visual image of an area of tissue surrounding a location in which to insert a screw (1202). In some examples, the obtaining the visual image may include performing lateral and anteroposterior (AP) radiographs, using fluoroscopy units to obtain various lateral and AP views (e.g., Ferguson's view, or other views), or using other x-ray or other imaging techniques. After the visual image is obtained, the visual image may be examined to confirm a pathology and identify the location in which to insert the screw (1204). The pathology may be a diagnosis (e.g., joint disruption, joint inflammation (e.g., degenerative sacroiliitis), or other diagnosis) determined from prior testing and imaging of the joint area. In some examples, identifying a location in which to insert the screw may include identifying surgical landmarks. In some examples, identifying a location in which to insert the screw also may include determining a position and trajectory for inserting a guide pin and a screw. Once a location is identified for inserting a screw, an incision may be created in the area of tissue surrounding the location (1206). In some examples, the incision may be approximately 2-3 cm long. In other examples, the length and location of the incision may vary depending on the size, dimensions, composition and/or geometry of the area of tissue, as may be sufficient for accessing a bone in the joint. For example, the length and placement of the incision may be different for a more obese patient (i.e., more posterior) than for a less obese patient. In some examples, the joint may be the sacroiliac joint, and the bone may be the ilium.

Once an incision is created, the area of tissue surrounding the location may be prepared for insertion of the screw, including placing a guide pin in the location, the guide pin configured to assist with placement of a drill guide, engaging a bone in the location with the drill guide, and drilling a pilot hole into the bone and an adjacent bone using the drill guide (1208). In some examples, the preparation of the area of tissue may also include separating the tissue at the incision to access the bone (i.e., the ilium). In some examples, the guide pin may be a medical grade sterile metal pin (e.g., Kirschner wire, Steinmann pin, or other metal pin) suitable for use in medical procedures. In some examples, placing a guide pin in the location may include aligning the guide pin (i.e., with the previously determined trajectory) and advancing the guide pin through a bone (i.e., the ilium), a joint (i.e., sacroiliac joint) and into an adjacent bone (i.e., sacrum) using a mallet. The guide pin should not touch, puncture, violate, or otherwise interfere with nerves and other sensitive or vulnerable tissue surrounding or adjacent to the joint (e.g., spinal canal, neuroforamen, anterior sacral cortical wall, sacral ala, or other tissue).

In some examples, engaging a bone in the location with a drill guide may include assembling a drill guide assembly having a pin sleeve and the drill guide, the pin sleeve having a trocar tip and configured to slide into the drill guide's cannula. In some examples, engaging a bone in the location with a drill guide also includes placing the drill guide assembly over the guide pin until the trocar tip rests against the bone. In some examples, engaging a bone in the location with a drill guide further includes unscrewing the pin sleeve while advancing the drill guide until the drill guide rests against the bone and the pin sleeve is backed away from the bone. In some examples, engaging a bone in the location with a drill guide also includes installing a striker tube over the pin sleeve and guide pin, onto the drill guide. In some examples, engaging a bone in the location with a drill guide further includes tapping the striker tube until the drill guide engages the bone. Once the drill guide engages the bone, the striker tube and pin sleeve may be removed.

In some examples, drilling a pilot hole into the bone (i.e., ilium) and an adjacent bone (i.e., sacrum) using the drill guide may include determining a drill depth using a drill depth gauge. In some examples, drilling a pilot hole into the bone and the adjacent bone also may include placing a drill bit stop collar over a cannulated adjustable drill bit according to the drill depth. In some examples, drilling a pilot hole into the bone and the adjacent bone further may include inserting the cannulated adjustable drill bit into the drill guide and over the guide pin. In some examples, drilling a pilot hole into the bone and the adjacent bone also may include drilling a hole through the bone, the joint and into the adjacent bone using the drill bit and a drill, the hole having the drill depth. Once the pilot hole is drilled, the drill and the cannulated adjustable drill bit may be removed.

Once the area of tissue is prepared for insertion of a screw, the screw may be inserted into the bone (i.e., ilium), the adjacent bone (i.e., sacrum) and a joint (i.e., sacroiliac joint) in between the bone and the adjacent bone, using the drill guide, including packing the screw with a material, inserting the screw into the drill guide, inserting a driver into the drill guide to engage the screw, and threading the screw into the pilot hole until the screw's head stops against the bone (1210). The inserted screw should not touch, puncture, violate, or otherwise interfere with nerves and other sensitive or vulnerable tissue surrounding or adjacent to the joint (e.g., spinal canal, neuroforamen, anterior sacral cortical wall, sacral ala, or other tissue). Once the screw is inserted into place, the driver, the guide pin and the drill guide may be removed (1212).

Figure 13A:
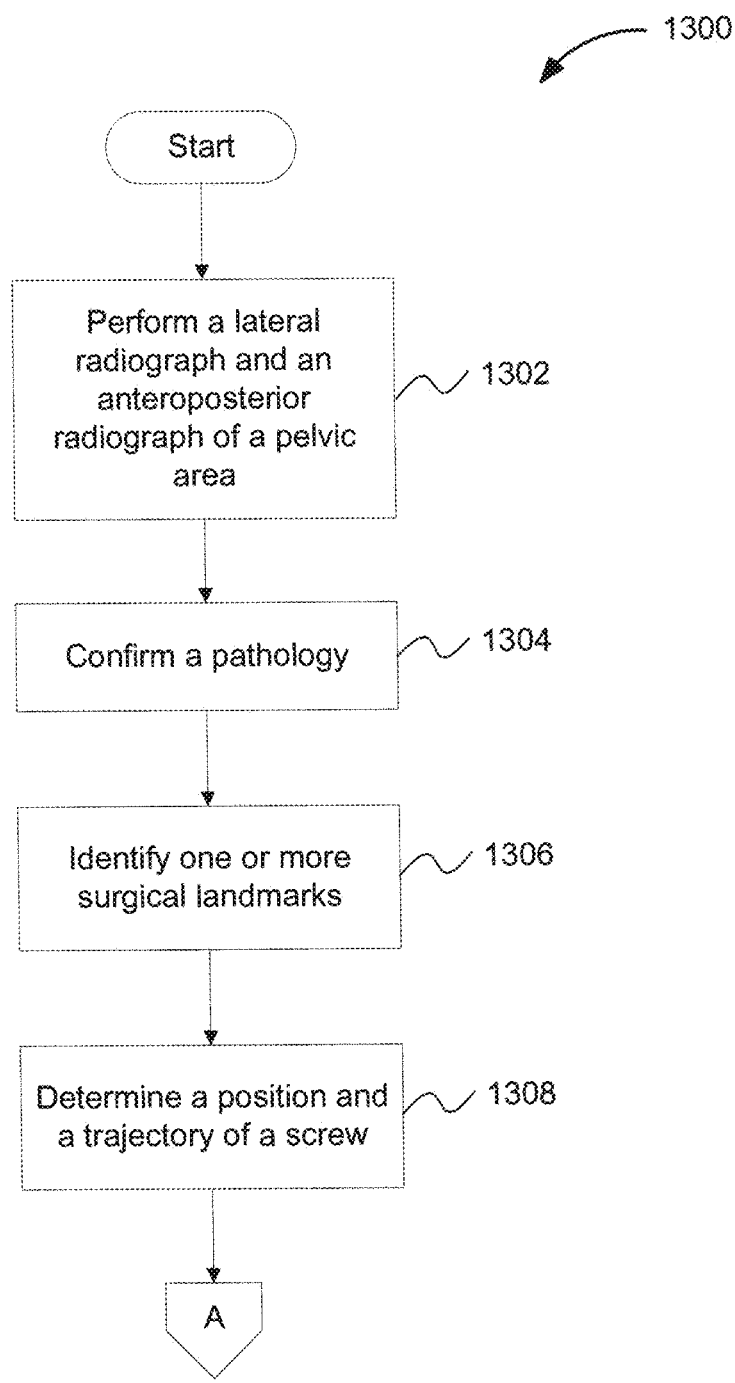
FIGS. 13A-F illustrate an exemplary process for fusion of a sacroiliac joint.

FIGS. 13A-F illustrate an exemplary process for fusion of a sacroiliac joint. FIG. 13A illustrates the pre-operative portion of process 1300. Here, process 1300 begins with performing a lateral radiograph and an anteroposterior (AP) radiograph of a pelvic area (1302). For example, a Ferguson's view may be obtained to view the sacroiliac joint and its surrounding tissue. In some examples, fluoroscopy techniques may be used to provide view or images in real time. Using the radiographs, a pathology is confirmed (1304) and one or more surgical landmarks are identified (1306). In some examples, identifying one or more surgical landmarks may include identifying a location for implantation of a screw. A position and a trajectory of the screw, or other implant, also may be determined (1308) pre-operatively.

Figure 13B:
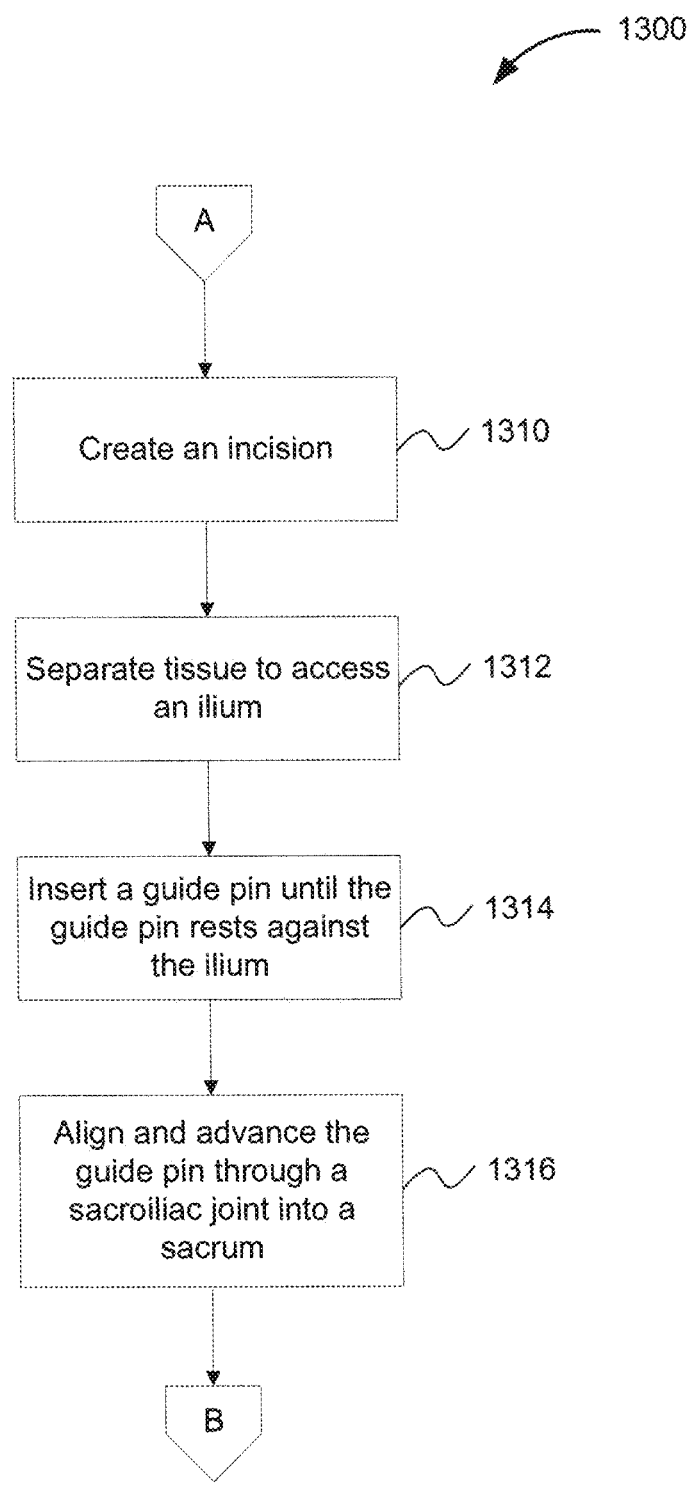

FIG. 13B illustrates the incision and guide pin placement portions of process 1300. The operation may begin with creating an incision (1310). In some examples, the incision may be approximately 2-3 cm long. In other examples, the length and location of the incision may vary depending on the size, dimensions, composition and/or geometry of a sacroiliac joint. For example, the length and placement of the incision may be different for a more obese patient (i.e., more posterior) than for a less obese patient. Once the incision is created, tissue may be separated to access the ilium (1312). Then a guide pin may be inserted until it rests against the ilium (1314). In some examples, the guide pin may be a medical grade sterile metal pin (e.g., Kirschner wire, Steinmann pin, or other metal pin) suitable for use in medical procedures. In some examples, the guide pin may be inserted through tissue near or adjacent to the ilium. Once the guide pin is resting against the ilium at the location of implantation, it may be aligned (i.e., according to the previously determined trajectory and position) and advanced through the sacroiliac joint into a sacrum (1316). In some examples, the guide pin may be advanced using a mallet. The guide pin should not touch, puncture, violate, or otherwise interfere with nerves and other sensitive or vulnerable tissue surrounding or adjacent to the joint (e.g., spinal canal, neuroforamen, anterior sacral cortical wall, sacral ala, or other tissue).

Figure 13C:
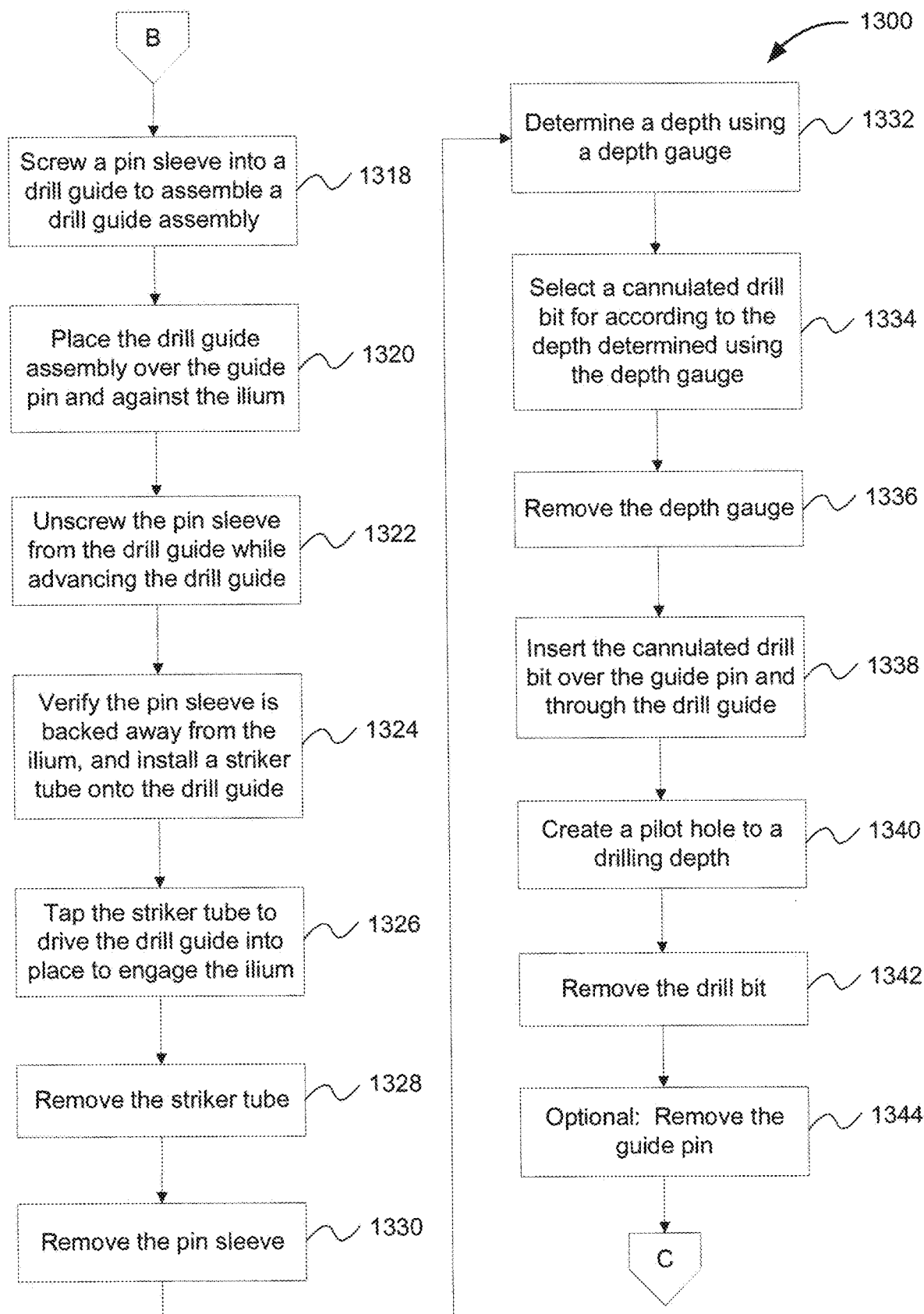

FIG. 13C illustrates the bone and joint preparation portion of process 1300. Once the guide pin is in place in the sacroiliac joint, a drill guide assembly may be prepared by screwing a pin sleeve into a drill guide (1318). In some examples, the outer diameter of the pin sleeve's shaft fits into the cannula of the drill guide, and is screwed into the drill guide so that the drill guide and pin sleeve are coupled securely. In some examples, the pin sleeve is screwed into the drill guide until the tip of the pin sleeve protrudes past the tip of the drill guide. The drill guide assembly may be placed over the guide pin and against the ilium (1320). In some examples, the drill guide assembly may slide over the guide pin until the tip of the drill guide assembly (i.e., the pin sleeve tip, which protrudes from the drill guide tip when the pin sleeve is fully screwed into the drill guide) rests against the ilium. Once the tip of the drill guide assembly is resting against the ilium, the pin sleeve may be unscrewed from the drill guide while the drill guide is advanced toward the ilium (1322). In some examples, the drill guide is advanced until the drill guide tip is resting against the ilium and the pin sleeve is out of the way (i.e., the pin sleeve tip is backed away from the ilium). In some examples, the pin sleeve is out of the way when the threads of the pin sleeve are entirely out of the drill guide head. Once it is verified that the pin sleeve is backed away from the ilium, a striker tube may be installed onto the drill guide (1324). In some examples, the striker tube may be installed by placing it over the portions of the guide pin and the pin sleeve extending out of the drill guide head, and onto the head of the drill guide, as shown in FIG. 5. Once the striker tube is installed onto the drill guide, the striker tube may be tapped to drive the drill guide into place to engage the ilium (1326). In some examples, the striker tube may be tapped using a mallet, suitable hammer, or other suitable tool for tapping the flat head of the striker tube. In some examples, the striker tube may be tapped more than once for the drill guide to engage the ilium. Once the drill guide engages the ilium, the striker tube may be removed (1328), and the pin sleeve also may be removed (1330). A depth gauge may then be used to determine a depth (1332). In some examples, the depth gauge may have numerically-labeled markings (e.g., depth markings 604a-604b) corresponding to depths (i.e., at 5 millimeter intervals). In some examples, the depth corresponds to a depth or distance that the guide pin is embedded into the bone. In some examples, the depth gauge fits over the guide pin and onto, or against, the drill guide, as shown in FIG. 6. Then, a cannulated drill bit may be selected according to the depth determined using the depth gauge (1334). In some examples, a cannulated drill bit for drilling an appropriate-sized pilot hole may be selected according to the depth of the guide pin. For example, if a guide pin has been inserted 40 mm deep into the sacroiliac joint, a cannulated drill bit configured to drill a pilot hole of 40 mm depth may be selected. In another example, a predetermined offset may be desired between the depth of the guide pin and the depth of the pilot hole, in which case a cannulated drill bit configured to drill a pilot hole of 40 mm minus the predetermined offset may be selected. In other examples, the cannulated drill bit may be adjustable. For example, an adjustable cannulated drill bit may have markings corresponding to the numerical depth readings on a depth gauge (e.g., depth gauge 602), the markings indicating a desired drilling depth (i.e., depth of a pilot hole). In this example, the adjustable cannulated drill bit may be fitted with a stop collar, as described herein, to stop the adjustable cannulated drill bit at the desired drilling depth. In some examples, a desired drilling depth may be the same as the depth of the guide pin. In other examples, the markings on a cannulated drill bit may account for a predetermined offset distance (e.g., 3 mm or other distance) from the depth of the guide pin. For example, if the guide pin is determined to be at a 40 mm depth, the 40 mm marking on the cannulated drill bit may correspond to a drilling depth of 37 mm. Once the cannulated drill bit is selected, or an adjustable cannulated drill bit is fitted with a stop collar at the desired marking, the depth gauge may be removed (1336) and the cannulated drill bit inserted over the guide pin into and through the drill guide (1338). In some examples, the cannulated drill bit fits snugly over the guide pin. Once the cannulated drill bit is in place within the drill guide, a pilot hole may be created to a drilling depth (1340). As described herein, the drilling depth may be the same as the depth of a guide pin as measured by the depth gauge, or it may be different. Once the pilot hole is created, the drill bit may be removed (1342). At this point, the guide pin may be removed optionally (1344), or it may be left in place as a guide for the screw insertion portion of process 1300.

Figure 13D:
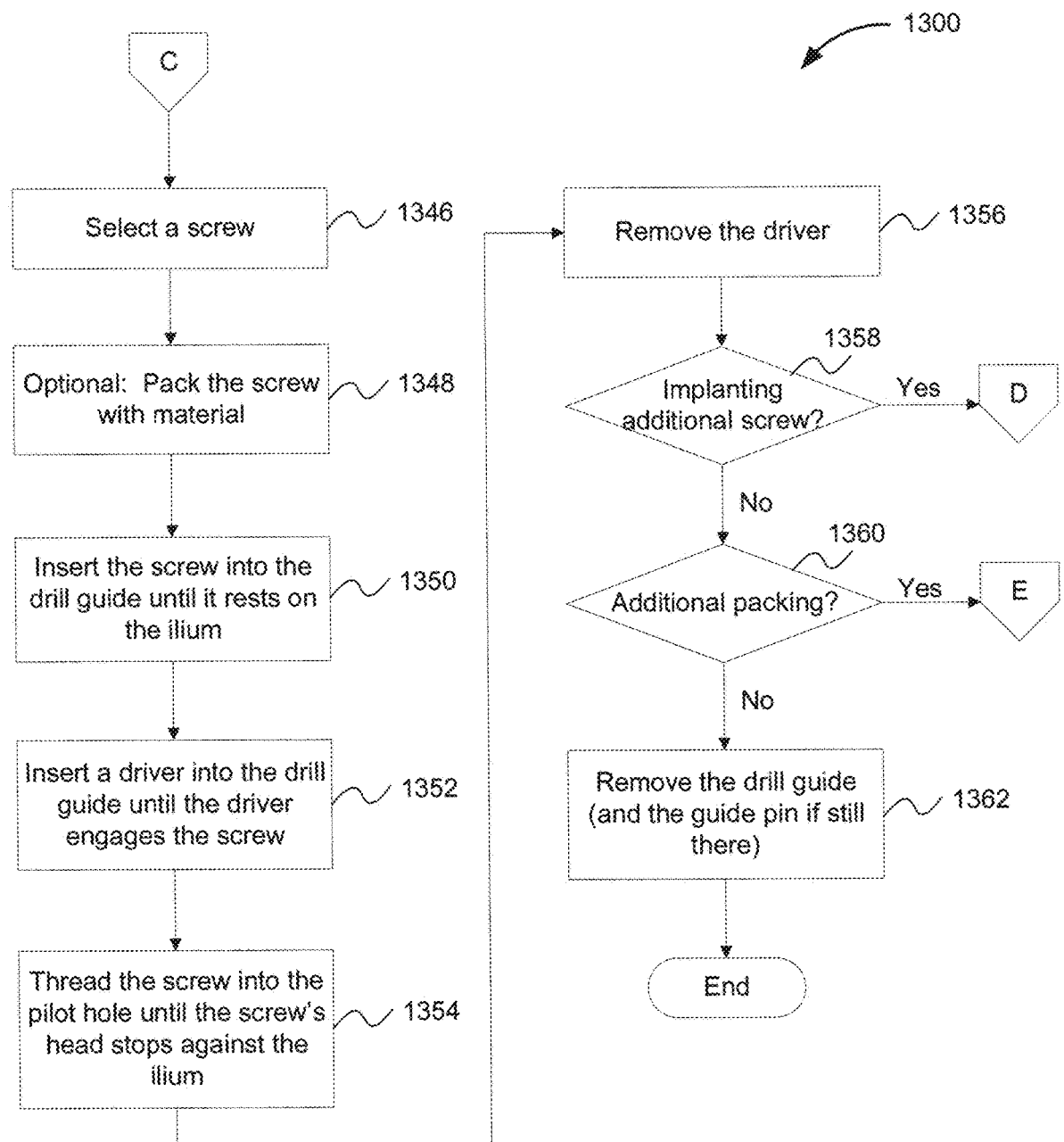

FIG. 13D illustrates the screw insertion portion of process 1300. A screw may be selected (1346), the screw having a length corresponding to the drilling depth. In some examples, the length of the screw may be the same as the drilling depth. In other examples, the length of the screw may be offset from the drilling depth by a predetermined distance (i.e., the screw length may be a few millimeters longer or shorter than the drilling depth. In some examples, the screw may be packed with material before being implanted (1348). In other examples, the screw may not be packed until after it is implanted. The screw may be inserted into a drill guide until the screw's tip rests against the ilium (1350). A driver may then be inserted into the drill guide until the driver engages the screw (1352). In some examples, the driver may be cannulated. In some examples, as described herein, the driver may be a TORX® or TORX®-like screwdriver. In other examples, the driver may be a different type of screwdriver, as may be appropriate for driving a screw with a different type of head (e.g., PHILLIPS™, slot, flat, Robertson, hex, or other type of screw head). In some examples, the driver may be hand operated. For example, the driver may be a hand operated manual driver, as shown in FIG. 9. In another example, the driver may be a powered driver. In still another example, the driver may be ratcheting, torque-limited, or have other characteristics useful for driving a screw into a joint. Using the engaged driver, the screw may be threaded into the pilot hole until the screw's head stops against the ilium (1354). The implanted screw should not touch, puncture, violate, or otherwise interfere with nerves and other sensitive or vulnerable tissue surrounding or adjacent to the joint (e.g., spinal canal, neuroforamen, anterior sacral cortical wall, sacral ala, or other tissue). Once the screw is driven into the pilot hole, and into place in the joint, the driver may be removed (1356). If no more screws are to be placed, and no additional or secondary packing of material into the screw is to be performed, then the drill guide may be removed, along with the guide pin if it has not been removed previously, at this time (1362).

Figure 13E:
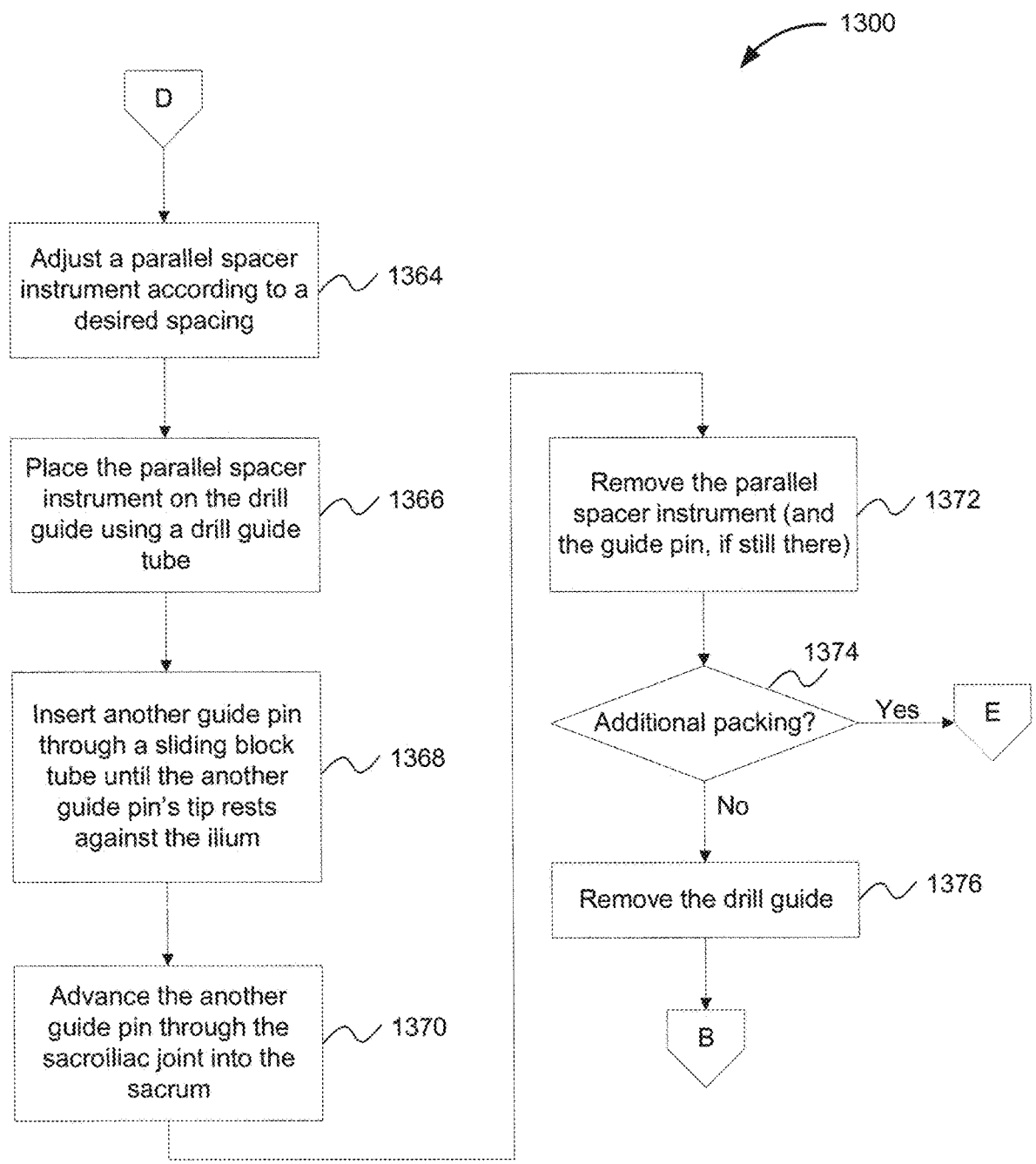

If additional screws are to be implanted, FIG. 13E illustrates portion of process 1300 wherein another guide pin is placed using the parallel spacer instrument. With the drill guide still in place from the previous screw insertion, a parallel spacer instrument is adjusted according to a desired spacing (i.e., between implanted screws) (1364), and is placed on the drill guide using a drill guide tube (1366). In some examples, the parallel spacer instrument may include a parallel spacer block with a drill guide tube, a sliding block with a sliding block tube, and a locking nut (as shown in FIGS. 10A-10D). In some examples, the parallel spacer instrument may be adjusted by sliding a sliding block to the desired spacing setting on the parallel spacer block, and tightening the locking nut to secure the sliding block in place (see FIGS. 10A-10D). In some examples, the sliding block may comprise a drill guide tube that fits into the shaft of a drill guide. In some examples, the drill guide tube may be cannulated to accommodate a guide pin. For example, if a previously-placed guide pin is still in the drill guide, the drill guide tube may slide over the guide pin and into the drill guide. Once the parallel spacer instrument is placed on the drill guide, another (i.e., a next) guide pin may be inserted through a sliding block tube until the tip of this next guide pin rests against the ilium (1368). This next guide pin may be advanced through the sacroiliac joint into the sacrum (1370), for example, using a mallet. In some examples, this next guide pin may be advanced through tissue before it rests on the ilium at the next location to implant a screw. This next guide pin should not touch, puncture, violate, or otherwise interfere with nerves and other sensitive or vulnerable tissue surrounding or adjacent to the joint (e.g., spinal canal, neuroforamen, anterior sacral cortical wall, sacral ala, or other tissue). Once this next guide pin is in place in the sacroiliac joint at this next location, the parallel spacer instrument may be removed (1372). If the previously-placed guide pin is still in the drill, it also may be removed at this time (1372). If no additional or secondary packing of material into the already-implanted screw is to be performed, then the drill guide may be removed from its current position (1374). The drill guide assembly may be re-assembled for repetition of the bone and joint preparation and screw insertion portions of process 1300 (see FIGS. 13C-13D) at the next location where the next (i.e., another) guide pin has been placed.

Figure 13F:
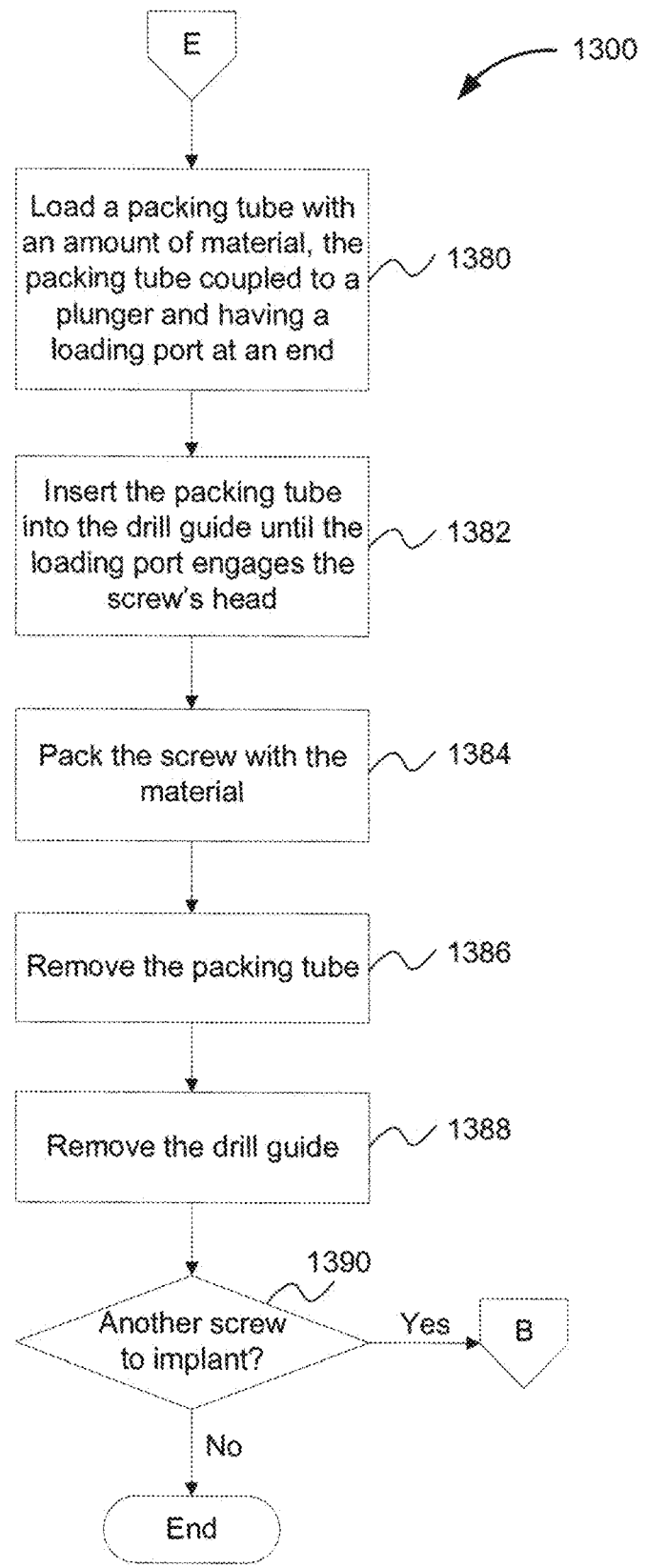

If additional or secondary packing of material into the already-implanted screw is to be performed, FIG. 13F illustrates the post-insertion packing portion of process 1300. A packing tube may be loaded with an amount of material, the packing tube coupled to a plunger and having a loading port at an end (1380), as shown in FIG. 11A. In some examples, the amount of material may correspond to a volume that fills or substantially fills the hollow shaft of a cannulated screw (i.e., the already-implanted screw), as described herein. Also as described herein, the material may include osteogenic compounds, osteoconductive materials, antibiotics, steroids, contrast materials, or other materials that may beneficial to fusing the joint, treating inflammation or other conditions in a joint, or enabling the visualization of the area within and adjacent to the screw. Once loaded, the packing tube may be inserted into the drill guide until the loading port engages the screw's head (1382). The screw then may be packed with said material (1384). In some examples, packing the screw may include depressing a plunger coupled to an end of a packing tube comprising a loading port at another end opposite to the plunger, the plunger configured to dispense said material out the loading port, for example into a cannulated screw (e.g., screws 100 and 200, or the like) coupled to the loading port, when depressed. A screw packed in such a way may in turn deliver said material into a joint through openings in the screw, as described herein. Once the screw is packed, the packing tube may be removed (1386). The drill guide then may be removed as well (1388). If there is another screw to implant (i.e., another guide pin has been placed using the parallel spacer instrument), then the drill guide assembly may be re-assembled for repetition of the bone and joint preparation and screw insertion portions of process 1300 (see FIGS. 13C-13D) at the next location. If no other screw is to be implanted, the wound created by the incision and the implantation process may be closed using standard surgical technique.

In other examples, processes 1200 and 1300 may be implemented with more or fewer steps. For example, electrical activity in a patient's body may be monitored during part or all of a joint fusion process (e.g., processes 1200 and 1300) using various techniques for measuring electrical potentials (e.g., somatosensory evoked potentials and other electrical potentials). In this example, electromyography (EMG) may be used to monitor electrical activity in muscles in the area surrounding, connected to, or otherwise associated with the joint (e.g., tibialis anterior, gastrocnemius, rectal sphincter, or other muscles). In another example, part or all of a joint fusion process (e.g., processes 1200 and 1300) may be performed under fluoroscopy guidance (e.g., providing a Ferguson's view of the sacroiliac joint). In some examples, processes 1200 and 1300 may be performed to implant multiple screws into a joint.

Although the foregoing examples have been described in some detail for purposes of clarity of understanding, the invention is not limited to the details provided. There are many alternative ways of implementing the invention. The disclosed examples are illustrative and not restrictive.

What is claimed:

1. A sacroiliac joint fusion system, comprising:
   a guide pin;
   a drill guide assembly, comprising
      a drill guide head having an opening and a rounded side; and
      a pin sleeve configured to receive the guide pin, wherein the guide pin guides placement of the drill guide assembly relative to a bone of a patient;
   a depth gauge comprising a plurality of depth markings configured to indicate a depth to which the guide pin is inserted into the bone;
   a striker tube including a distal edge having a first segment that removably encircles a portion of the rounded side of the drill guide head and a second segment that removably abuts a proximal side of the drill guide head, the first segment being disposed on a different plane than the second segment.

2. The system of claim 1, wherein the drill guide assembly further comprises a drill guide contact marking configured to indicate an edge of the depth gauge to be placed into the drill guide.

3. The system of claim 1, wherein the depth markings account for a length of the drill guide and a length of the guide pin.

4. The system of claim 2, wherein the depth markings indicate the depth that the guide pin has been inserted into a bone relative to the drill guide when the depth gauge is placed over the guide pin and the drill guide contact marking is in contact with the drill guide head.

5. The system of claim 1, wherein the depth gauge has a guide pin receiving element that receives the guide pin.

6. The system of claim 5, wherein the guide pin receiving element slides over the guide pin and the drill guide contact marking contacts the drill guide head.

7. The system of claim 1, wherein the depth markings indicate a range of the depth to which the guide pin is inserted into the bone.

8. The system of claim 7, wherein the depth markings indicate a range 20-50 millimeter depths to which the guide pin is inserted into the bone.

9. The system of claim 1, wherein the depth markings include a numeric indicator corresponding to the depths to which the first guide pin is inserted into the bone.

10. The system of claim 1, wherein the depth gauge markings indicate a depth to which a pilot hole is drilled into the bone.

11. The system of claim 1, further comprising an implant configured to form a conduit in a sacroiliac joint to at least partially fuse the sacroiliac joint.

12. The system of claim 11, wherein the depth gauge markings indicate a depth to which the implant is implanted into the bone.

* * * * *